(12) United States Patent
Hofmann

(10) Patent No.: US 8,979,793 B2
(45) Date of Patent: Mar. 17, 2015

(54) METHODS AND DEVICES FOR PERCUTANEOUS AND SURGICAL INTERVENTIONS

(76) Inventor: Lawrence Hofmann, Stanford, CA (US)

(*) Notice: Subject to any disclaimer, the term of this patent is extended or adjusted under 35 U.S.C. 154(b) by 228 days.

(21) Appl. No.: 13/040,126

(22) Filed: Mar. 3, 2011

(65) Prior Publication Data

US 2011/0245751 A1    Oct. 6, 2011

Related U.S. Application Data

(62) Division of application No. 10/498,035, filed as application No. PCT/US03/02186 on Jan. 24, 2003, now abandoned.

(60) Provisional application No. 60/351,516, filed on Jan. 24, 2002.

(51) Int. Cl.
| | |
|---|---|
| *A61M 1/02* | (2006.01) |
| *A61B 17/22* | (2006.01) |
| *A61B 17/34* | (2006.01) |
| *A61M 25/00* | (2006.01) |
| *A61M 39/06* | (2006.01) |

(52) U.S. Cl.
CPC ....... *A61B 17/22* (2013.01); *A61B 2017/22069* (2013.01); *A61B 2017/3488* (2013.01); *A61B 2217/005* (2013.01); *A61M 25/0017* (2013.01); *A61M 39/06* (2013.01)
USPC ..... 604/103.03; 604/174; 604/264; 604/5.01; 604/509; 606/108

(58) Field of Classification Search
USPC ............... 606/108, 151–156, 192, 194, 200; 604/4.01, 5.01, 6.06, 6.09, 6.11, 6.16, 604/7–10, 101.01, 101.03, 101.05, 103, 604/103.03, 174, 265, 6.01, 509; 600/184
See application file for complete search history.

(56) References Cited

U.S. PATENT DOCUMENTS

| | | | |
|---|---|---|---|
| 3,866,599 A | | 2/1975 | Johnson |
| 3,882,852 A | | 5/1975 | Sinnreich |
| 4,230,119 A | | 10/1980 | Blum |
| 4,475,899 A | | 10/1984 | Muller |
| 4,712,551 A | * | 12/1987 | Rayhanabad ............... 604/8 |
| 4,836,204 A | | 6/1989 | Landymore et al. |
| 5,041,093 A | | 8/1991 | Chu |
| 5,295,958 A | * | 3/1994 | Shturman ............ 604/103.07 |
| 5,312,341 A | | 5/1994 | Turi |
| 5,470,313 A | * | 11/1995 | Crocker et al. ......... 604/103.07 |
| 5,509,900 A | | 4/1996 | Kirkman |

(Continued)

OTHER PUBLICATIONS

Proxis Embolic Protection System Product Literature, 2 pages (2004).

*Primary Examiner* — Kathleen Holwerda
(74) *Attorney, Agent, or Firm* — Locke Lord LLP; Gabriel J. McCool

(57) ABSTRACT

Methods and devices for performing percutaneous and surgical interventions. The devices comprising a tubular portion and retractable mechanism at the distal end of the tubular portion. The retractable mechanism prevents the device from pulling out of an anatomical structure during complex interventions, for example, when switching from an antegrade to a retrograde approach within a blood vessel, enables the use of a single sheath when declotting AV hemodialysis fistulas and can provide occlusion of blood flow during interventions and means of removal of debris or clot from the blood vessel.

18 Claims, 18 Drawing Sheets

(56) References Cited

U.S. PATENT DOCUMENTS

| | | | |
|---|---|---|---|
| 5,542,434 A * | 8/1996 | Imran et al. | 600/585 |
| 5,792,118 A | 8/1998 | Kurth et al. | |
| 6,048,331 A * | 4/2000 | Tsugita et al. | 604/102.03 |
| 6,051,014 A | 4/2000 | Jang | |
| 6,161,547 A * | 12/2000 | Barbut | 128/898 |
| 6,277,136 B1 | 8/2001 | Bonutti | |
| 6,295,989 B1 * | 10/2001 | Connors, III | 128/898 |
| 6,423,032 B2 * | 7/2002 | Parodi | 604/103.07 |
| 6,451,042 B1 | 9/2002 | Bonutti | |
| 6,540,712 B1 * | 4/2003 | Parodi et al. | 604/6.14 |
| 6,589,214 B2 * | 7/2003 | McGuckin et al. | 604/175 |
| 6,830,579 B2 * | 12/2004 | Barbut | 606/200 |
| 2005/0267323 A1 | 12/2005 | Dorros et al. | |

\* cited by examiner

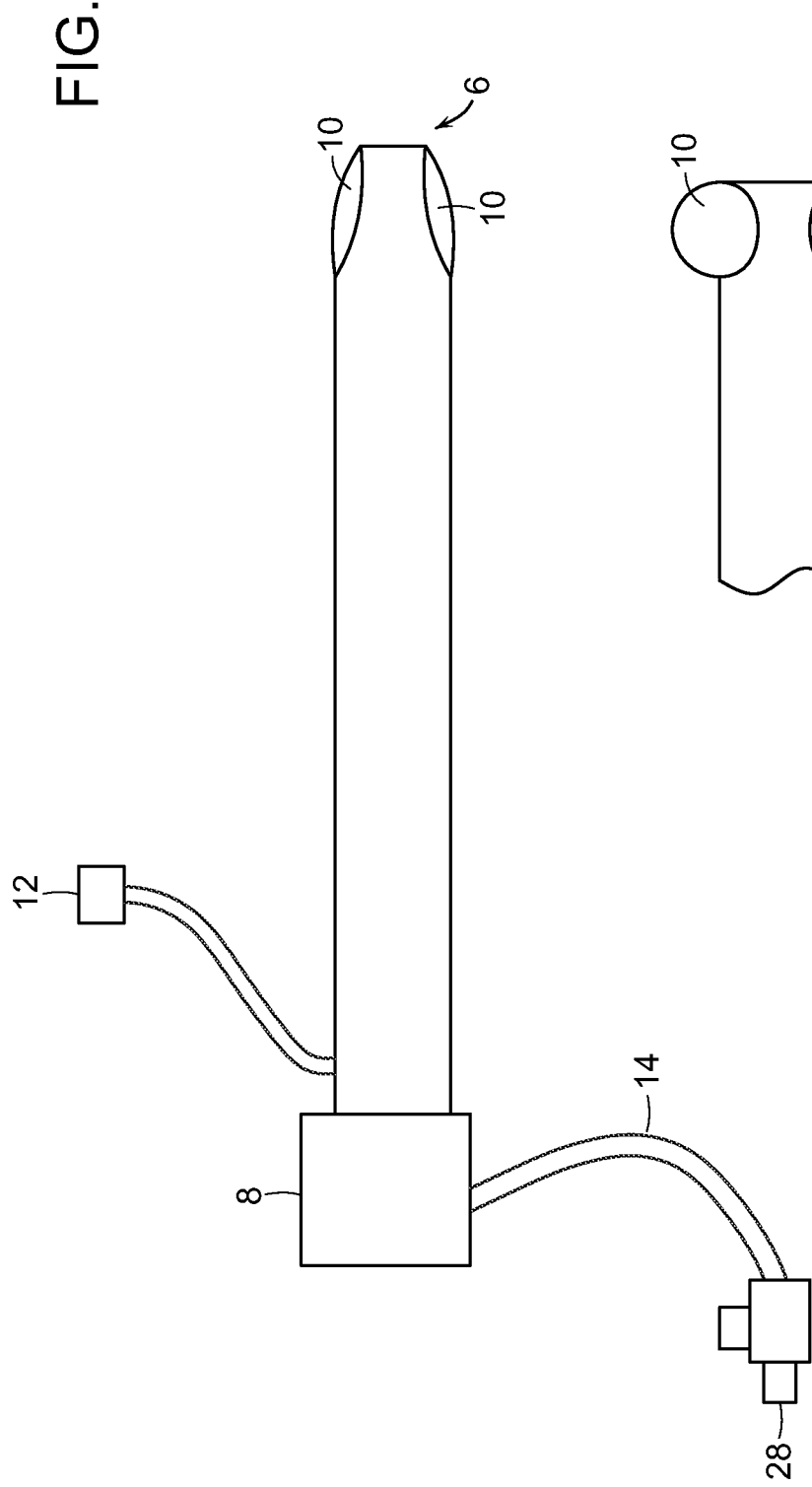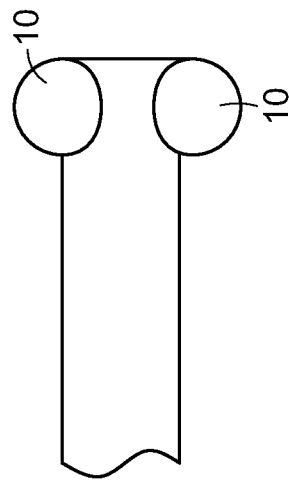

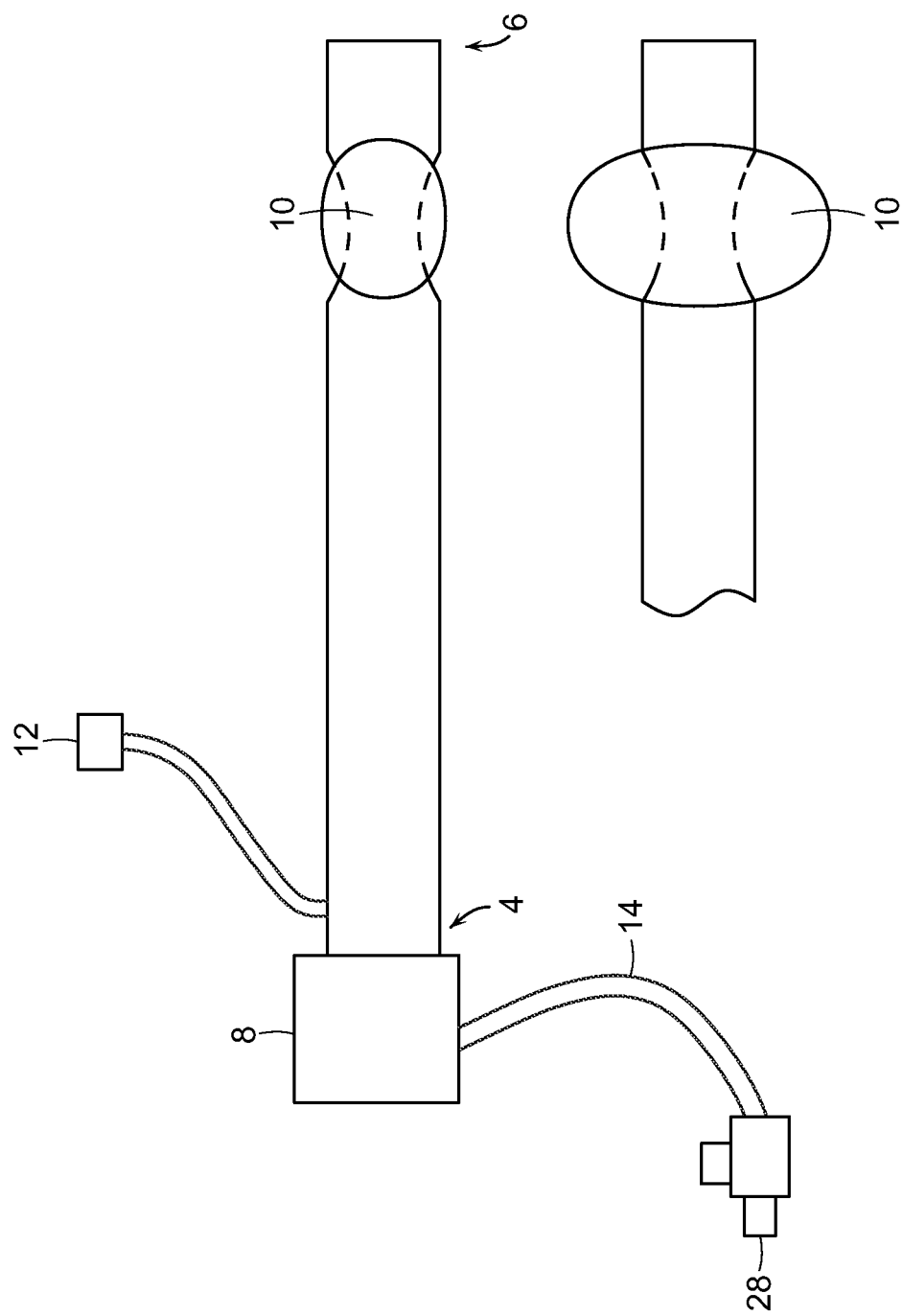

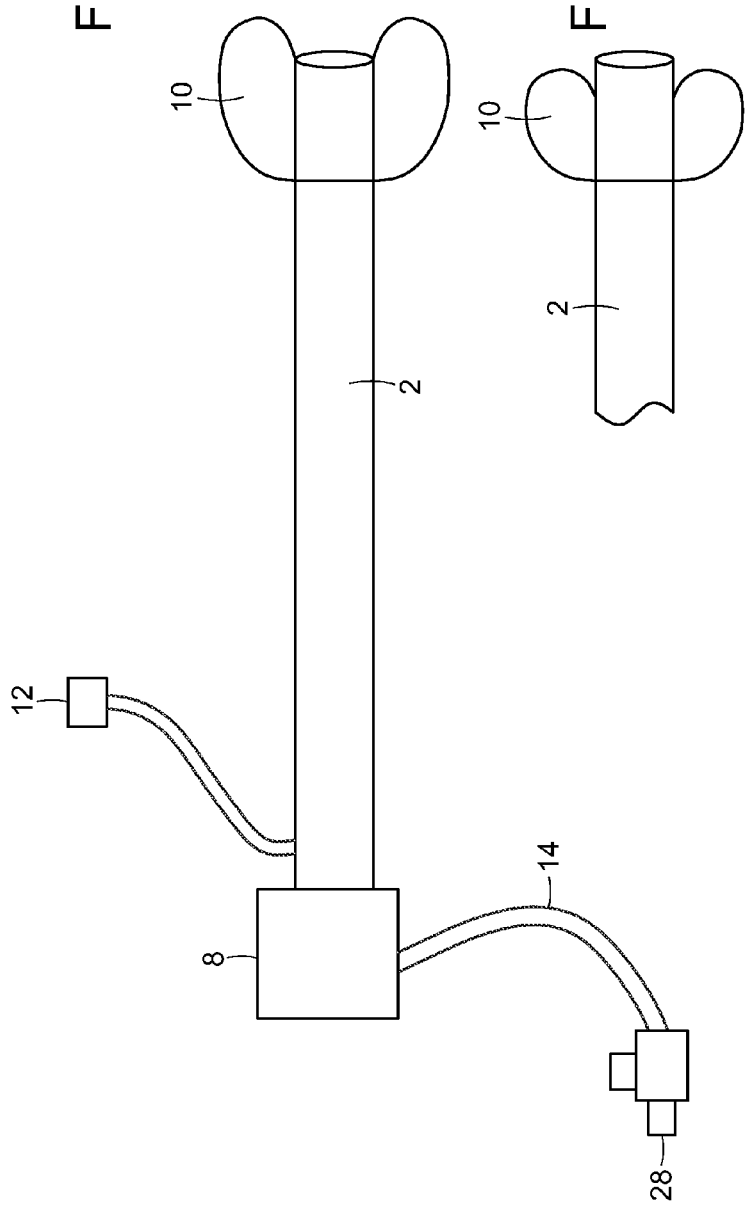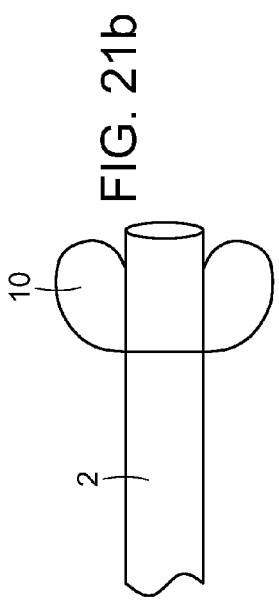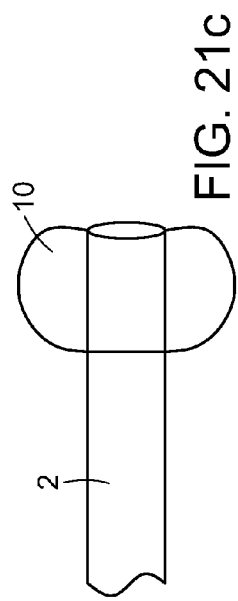

METHODS AND DEVICES FOR PERCUTANEOUS AND SURGICAL INTERVENTIONS

CROSS-REFERENCE TO RELATED APPLICATIONS

This application is a divisional of U.S. application Ser. No. 10/498,035, which is a national entry of International Application PCT/US2003/02186 having an International filing date of Jan. 24, 2003, which claims priority to U.S. Provisional Application No. 60/351,516, as filed on Jan. 24, 2002. The disclosures of each of these Applications are incorporated herein by reference in their entireties.

The present invention generally relates to methods and devices for performing percutaneous and surgical interventions. More particularly, the present invention provides improved vascular sheaths and guide catheters and methods of use.

BACKGROUND OF THE INVENTION

Vascular sheaths and guide catheters are used routinely in interventional radiology and interventional cardiology. The sheath serves as a conduit from the skin surface to the artery to allow passages of catheters, guide wires, stents, angioplasty balloons and similar instruments through the subcutaneous track without damaging the surrounding tissues or the blood vessel itself. The sheath is generally composed of four main components. The first is the tubular portion, which is the conduit from the skin surface into the blood vessel. The second portion is a hemostatic valve on the skin surface portion of the sheath. The third component is a sidearm tubing with a stopcock that allows the sheath to be flushed or aspirated with fluid. The fourth component is a tapered dilator that passes through the tubular portion of the sheath to allow a non-traumatic introduction of the sheath into the blood vessel. Once the sheath is introduced into the blood vessel, the dilator is then removed to allow passages of catheters. These sheaths are used in over 99 percent of all vascular cases. The vascular sheaths are generally used by first puncturing the blood vessel with a needle, followed by insertion of a guide wire. A dilator, having mounted in the vascular sheath, is then advanced into the blood vessel over the guide wire. The dilator is removed, leaving the distal end of the vascular sheath inside the blood vessel.

While these current vascular sheaths and methods are generally suitable, they have many drawbacks.

The designs of current vascular sheaths do not adequately maintain the sheaths steadily in the blood vessel. For example the sheaths can be easily pulled out of the blood vessel during manipulations of catheters and other devices within the lumen of the sheath.

Further, when using vascular sheaths to perform surgery on carotid artery stenosis, emboli may form during the course of the procedure. These emboli can flow into the cerebral vasculature, leading to ischemic stroke. Current sheaths do not adequately prevent the flow of emboli into the cerebral vasculature.

Still further, during a number of vascular procedures, it would be advantageous to reposition the sheath from a retrograde position (against the blood flow) to an antegrade position (with the blood flow) or visa-versa. For example, when placing a stent in a vessel, performing an angioplasty or performing a thrombectomy, a vascular sheath is inserted to the treatment location using a retrograde common femoral arterial approach. However, during such procedures, it is often discovered that there are a plurality of treatment locations. For example, in performing an angioplasty procedure on an obstructed vessel, it is not uncommon to find that the vessel is obstructed at more than one location. For example, one location may be located upstream from the insertion point of the vascular sheath and another location may be located downstream from the insertion point of the vascular sheath. Thus, it would be very desirable to be able to position the vascular sheath in a retrograde position to treat the first location, followed by repositioning of the vascular sheath in an antegrade position to treat the second location. This is extremely difficult to do with the current sheath technology. These sheaths pull out of the vessel when the operator tries to redirect the sheath, and the operator loses vascular access. Thus, with current sheath designs, the first location is first treated by making an incision to provide retrograde access to the first obstructed location. After the first location is treated, the sheath is removed and the puncture in the vessel must be allowed to heal prior to treatment of the second obstructed location. It can take as long as a week for the puncture in the vessel to heal. The patient must then return for a second procedure to treat the second obstructed location, which requires a second incision.

Additionally, current methods for Fogarty balloon thrombectomy require a surgical incision of the blood vessel and clamping of the blood vessel distal to the incision (for an iliac artery thrombectomy). The balloon is passed to the superior most aspect of the clot, inflated and pulled inferiorly, dragging the clot to the arteriotomy site and out of the blood vessel. If the same aforementioned procedure were performed percutaneous with current sheath technology, the size mis-match between the blood vessel and the sheath would cause the clot to flow past the sheath and into the distal blood vessels.

Thus, any improvements in vascular sheaths would be desirable.

SUMMARY OF THE INVENTION

The present invention provides improved devices for performing percutaneous and surgical interventions, particularly vascular sheaths and guide catheters, and methods of use thereof. More particularly, the present invention provides a device that may be manipulated within an anatomical structure while eliminating the possibility of the device losing access to the anatomical structure during such manipulation.

For example, in one embodiment, the device comprises a vascular sheath or a guide catheter that may be inserted and repositioned within a blood vessel while eliminating the possibility of losing vascular access during such manipulation. In one embodiment, the vascular sheath or guide catheter may be repositioned from a retrograde to an antegrade position in a blood vessel, and vice versa, while eliminating the possibility of losing vascular access during such manipulation.

The devices of the present invention can be used during all types of percutaneous interventions and surgical interventions including, for example, vascular percutaneous interventions such as thrombectomies, carotid stenting, hemodialysis AV fistula declotting, superficial femoral artery interventions, pelvic vasculature stenting, and biliary interventions and kidney stone extraction.

In an exemplary embodiment, the device includes a tubular portion having a proximal end and a distal end. During use, at least a portion of the device is inserted into an anatomical structure distal end first. Located near the distal end of the tubular portion is a mechanism that prevents the device from losing access to the anatomical structure during manipulation of the device. At least one lumen further extends along the length of the tubular portion from the proximal end to the distal end. The lumen is designed so that materials can be removed from and added to the anatomical structure through the lumen. For example, emboli, blood clots and other materials can be evacuated from a blood vessel using an aspiration technique or by pulling clot or other material out through the sheath by means of a Fogarty balloon, and agents, such as medicaments, anticoagulants and contrast media may be injected into the blood vessel. In embodiments wherein the device is a vascular sheath, the lumen is sized so that various instruments may be inserted through the sheath to the treatment site. In embodiments wherein the device is a guide catheter, the lumen is also sized so that various instruments may be inserted through the sheath to the treatment site.

In some embodiments, for example, wherein the device is a vascular sheath, a hemostatic valve is located at the proximal end of the tubular portion. In some embodiments, the hemostatic valve is removable. A side arm in fluid communication with the lumen can further be located near the proximal end of the tubular portion to allow emboli, blood clots and other materials to be evacuated from the blood vessel through the tubular portion and to allow agents, such as medicaments, anticoagulants and contrast media to be injected into the blood vessel through the tubular portion. In some embodiments, a tapered dilator further passes from the distal end to the proximal end through the tubular portion. In devices used for balloon thrombectomy, a silicon pinch valve would further be included near the proximal end of the tubular portion.

The mechanism that prevents the device from losing access to the anatomical structure during manipulation of the device can vary.

In one embodiment, the mechanism is an inflatable balloon located at or near the distal end of the tubular portion. The inflatable balloon can be designed to inflate to a variety of shapes and sizes. For example, in one embodiment, the inflatable balloon inflates to an overall round or oval shape and is situated coaxial with the tubular portion. In another embodiment, the inflatable balloon inflates to a funnel-like shape coaxial with the tubular portion, wherein the smaller cross-section of the funnel-like shaped balloon is towards the proximal end of the tubular portion and the larger cross-section of the funnel-like shaped balloon is towards the distal end of the tubular portion. In yet another embodiment, a plurality of inflatable balloons are positioned to inflate about the outer circumference of the tubular portion.

In embodiments wherein the mechanism is in the form of one or more inflatable balloons, one or more inflation ports are further located near the proximal end of the tubular portion for inflation of the one or more balloons. The one or more inflation ports are in communication with the one or more balloons via, for example, one or more inflation channels extending from the inflation port(s) to the balloon(s) through the wall of the tubular portion.

In another embodiment, the mechanism comprises one or more retractable extensions near the distal end of the tubular portion. For example, two or more retractable arm-like extensions may be located near the distal end of the tubular portion. These retractable extensions are remotely deployed and retracted by a user of the device with a deployment/retraction mechanism located near the proximal end of the device. During insertion of the device into the anatomical structure, these extensions would be retracted (e.g. housed within the tubular portion or folded back against the side surfaces of the tubular portion) such that the cross section of the tubular portion is not significantly increased during insertion of the device. As used herein, no "significant" increase in the cross-section of the tubular portion means that the mechanism does not over-dilate the arteriotomy (the incision in the anatomical structure through which the device is inserted). Upon insertion of the device into the anatomical structure to the desired site, the extensions could then be deployed.

The device of the present invention provides a number of advantages over prior devices. For example, by forming the device with a mechanism, such as a balloon or one or more extensions, at the distal end of the tubular portion, the mechanism prevents the device from pulling out of a anatomical structure during complex interventions, for example, when switching from a retrograde to an antegrade approach within a blood vessel (i.e. from a position pointing towards the head to a position pointing towards the feet) and vice versa.

Use of balloon or extension mechanisms further enables the use of a single device when declotting AV hemodialysis fistulas.

The device of the present invention also serves as a protection device during any number of procedures. For example, during use of the device in a blood vessel, the mechanism on the distal end of the device can be deployed to provide occlusion of antegrade blood flow during interventions and protect against embolization. For example, during the placement of an internal carotid artery stent, using current vascular sheaths, the antegrade blood flow can cause embolic material to propagate into the intracerebral circulation, thereby causing a stroke. By inflating the one or more balloons in the carotid artery in accordance with the present invention, or, for example, by deploying one or more extensions that occlude the blood vessel, antegrade flow can be prevented. Retrograde flow would be provided from the contralateral carotid artery. Similarly, during percutaneous coronary interventions in either native vessels or bypass grafts, inflation of the balloon serves as a protection device, preventing distal emboli from propagating forward. In addition, during a suction thrombectomy, if a clot has lodged in a blood vessel, antegrade flow will apply a pressure head to keep the clot lodged in its position. By occluding the lumen with the balloon or extension mechanisms on the sheath, back-bleeding causes the clot to propagate towards the vascular sheath, and the clot can be aspirated through the vascular sheath or pulled through the vascular sheath using a Fogarty balloon. Still further, the balloon or extension mechanisms can also prevent blood flow from passing through the blood vessel, which is advantageous during thrombectomy to prevent embolic material from propagating downstream.

During each of these procedures, after occlusion of the vessel, the embolic material, clot or other materials in the blood vessel could then be aspirated through the vascular sheath or pulled through the vascular sheath using a Fogarty balloon.

Alternatively, during each of these procedures, after occlusion of the vessel, a continuous flow reversal could be created. For example, a continuous flow reversal could be created by forming a circuit from the blood vessel, through the distal end of the tubular portion, through the tubular portion, and into a target vessel. This would require vascular access to the target vessel. Such continuous flow reversal would be useful, for example, in performing a procedure wherein materials, for example emboli, blood clots, or blood, are transferred from a donor blood vessel into a recipient blood vessel. For example, the device could be used to occlude a donor vessel and prevent emboli, blood clots and other materials from propagating into the coronary vasculature, followed by transfer of the emboli, blood clots and other materials to a recipient blood vessel wherein the danger of having the materials propagate into the coronary vasculature is eliminated. In this embodiment, the vascular sheath would be inserted in the donor blood vessel and, a continuous flow reversal could be created by forming a circuit between the "donor" vessel housing the embolic material to a "recipient" vessel elsewhere in the body. The circuit, thus, would extend from the distal portion of the tubular portion, through the tubular portion, and into a recipient vessel. Vascular access to the recipient vessel could be provided, for example, by a tube, a guide catheter or a vascular sheath. Thus, for example, a vascular sheath in accordance with the present invention could be inserted in the donor vessel, and the side-arm of the vascular sheath could be connected to the recipient vessel, for example, via tubing or via a second vascular sheath or a guide catheter. In some embodiments, a pumping mechanism is interposed in the circuit between the donor and recipient vessels to assist in reversing the blood flow.

Preferably, during the continuous flow reversal procedure, the balloon or extensions could be retracted or partially retracted at any point in the procedure to allow reperfusion of blood flow through the blood vessel.

Continuous flow reversal could also be useful in a procedure wherein blood is transferred from one patient to another, or from one site in a patient to another site in the same patient either during cardiac bypass surgery or during carotid artery surgery. In such procedures, the device of the present invention, for example, in the form of a vascular sheath or guide catheter, would be inserted into a donor vessel. The device of the present invention would then be connected to a recipient vessel via, for example, a tube, conventional guide catheter, conventional vascular sheath, or second device in accordance with the present invention. The device of the present invention would be particularly helpful on preventing the loss of vascular access during the blood transfer procedure.

Methods in accordance with the present invention comprise making a small incision in the upper thigh or other insertion site to provide access to the target location. The device of the present invention is then inserted into the anatomical structure. For example, when the anatomical structure is a blood vessel, a needle is introduced through the incision into the blood vessel. A guide wire is then inserted through the needle into the blood vessel using a retrograde approach. The device is then inserted over the guide wire and is passed into the blood vessel to a desired depth using a retrograde approach. In embodiments wherein the device is guide catheter, a vascular sheath is typically first inserted and the guide catheter is inserted through the vascular sheath. In embodiments wherein the device is a vascular sheath, the vascular sheath with dilator in the central lumen is inserted over the guide wire and is passed into the blood vessel to a desired depth using a retrograde approach. The guide wire and dilator are removed and the vascular sheath remains positioned in the blood vessel. Once the device is positioned within the anatomical structure, the mechanism is then activated, e.g. by inflating the balloon(s) at the distal end of the tubular portion through the inflation port or deployment of the extension(s). If a procedure requiring the blood vessel to be occluded is being performed, the one or more balloons are inflated until the vessel is completely occluded. Further, the one or more extensions can be designed such that the vessel can be completely occluded by the extensions, by, for example, forming the one or more extensions to extend outwards from the tubular portion in a circle arrangement or a funnel-like arrangement.

To aspirate emboli, blood clots and other materials from a blood vessel, an aspiration device is connected to the device, for example, an aspiration device may be connected to the vascular sheath through the side-arm, and the material(s) aspirated from the blood vessel, through the tubular portion and out of the device. If agents are to be injected into the anatomical structure, e.g. a blood vessel, a syringe or similar injection mechanism is connected to the device, for example, to the side-arm of a vascular sheath, and the agent is injected through the device into the anatomical structure. In embodiments wherein the device is a vascular sheath, various devices such as, for example, catheters, guide wires, stents, angioplasty balloons and similar instruments can also be inserted through the tubular portion for various procedures.

If the surgeon wishes to reposition the device to an antegrade position so that the surgeon can, for example, perform a thrombectomy on the other side of the puncture site into the blood vessel, the surgeon inflates or deflates the balloon(s) such that the cross-section of the tubular portion plus balloon(s) is smaller than the diameter of the blood vessel and larger than the arteriotomy (the incision in the blood vessel through which the device was inserted) and simply pulls the device back towards the insertion point. The device is then pulled outwards through the incision, but not completely out of the incision. Then, the device is manipulated and pushed back into the blood vessel in an antegrade position. The device can, likewise, be repositioned from an antegrade to a retrograde position. In the embodiment where the mechanism comprises one or more extensions, the surgeon, likewise, deploys the extension(s) such that the cross-section of the tubular portion of the device plus extension(s) is smaller than the diameter of the blood vessel and larger than the arteriotomy (the incision in the blood vessel through which the vascular sheath was inserted) and simply pulls the device back towards the insertion point. The device is then pulled outwards through the incision, but not completely out of the incision. Then, the device is manipulated and pushed back into the blood vessel in an antegrade position, possibly over a guide wire with the dilator in the central lumen of the device. The sheath can, likewise, be repositioned from an antegrade to a retrograde position. In the above procedures, the balloon(s) or extension(s) prevent the device from being completely withdrawn from the blood vessel, so that the operator can manipulate the device without the concern of losing vascular access.

Methods of the invention also include use of the device to provide occlusion of antegrade blood flow during interventions and protect against embolization.

For example, in one embodiment, the device is inserted into the blood vessel and the mechanism (i.e. balloon(s) or extension(s)) is deployed until the vessel is occluded and antegrade blood flow is prevented. An internal carotid artery, coronary artery, or renal artery stent can then be placed within the vessel. By preventing antegrade blood flow, the mechanism will prevent embolic material from propagating into the intracerebral circulation.

In another embodiment, during percutaneous coronary interventions in either native vessels or bypass grafts, deployment of the mechanism (i.e. balloon(s) or extension(s)) to occlude the vessel functions to prevent distal emboli from propagating forward.

In another embodiment, during a suction thrombectomy, the mechanism (i.e. balloon(s) or extension(s)) is deployed to occlude the vessel, thereby causing back-bleeding. The back-bleeding will then cause any clots lodged in the blood vessel to propagate towards the device. The clot can then be removed by aspirating it through the device or pulling it through the device using a Fogarty balloon.

In yet another embodiment, the mechanism (i.e. balloon(s) or extension(s)) can be deployed during a thrombectomy to prevent blood flow from passing through the blood vessel and around the device, which, in turn, prevents embolic material from propagating downstream.

In yet another embodiment, the device of the present invention could be used to create continuous flow reversal. For example, the device of the present invention is inserted in a target blood vessel and is also connected to a recipient blood vessel, such that materials could be transferred from the target blood vessel into the recipient blood vessel. In this embodiment, vascular access to the recipient vessel would be required. For example, the device of the present invention could be connected to tubing, to a conventional guide catheter, to a conventional vascular sheath, or to a second device in accordance with the present invention, which, in turn is inserted in the recipient blood vessel. The continuous flow reversal could then be used to transfer materials, such as clots and embolic materials, from a target vessel where there is a risk that the materials will propagate to the coronary or cerebral vasculature to a recipient vessel wherein this risk is eliminated. The continuous flow reversal could also be used to simply transfer blood from a target vessel to a recipient vessel, for example, in performing a blood transfer from one patient to another.

During the continuous flow reversal, the mechanism may be deployed to occlude the vessel, for example, if there is a risk that clots and embolic material may propagate to the cerebral vasculature. Alternatively, the mechanism may be deployed not to occlude the vessel, but, rather, to maintain vascular access if, for example, there is minimal risk that clots and embolic material may propagate to the cerebral vasculature. If the mechanism is deployed to occlude the vessel, the method of continuous flow reversal may further include reperfusion of blood. For example, if reestablishment of the flow of blood to the heart is desired for a period of time during the procedure, the mechanism may be retracted during the procedure so that the vessel is no longer occluded and blood flow is reestablished. After perfusion of the blood is reestablished for a desired period of time, the mechanism may again be deployed to occlude the vessel. In some embodiments, during reperfusion, the circuit between the target blood vessel and recipient blood vessel can be blocked so that reperfusion is carried out while transfer of materials from the donor to recipient blood vessel is stopped. Then, after perfusion of the blood is reestablished for a desired period of time, the circuit may then be opened to continue transfer of materials from the donor to recipient blood vessel. During this time, the vessel may remain not occluded or may again be occluded by redeployment of the mechanism.

Other aspects and embodiments of the invention are discussed infra.

BRIEF DESCRIPTION OF THE DRAWINGS

FIG. 19a-b show a shows a side view of a device for performing percutaneous and surgical interventions having a tapered distal end into which one or more mechanisms are retracted (19a) and deployed (19b) in accordance with one embodiment of the present invention.

FIG. 20a-b show a side view of a device for performing percutaneous and surgical interventions having a tapered section along its length end into which one or more mechanisms are retracted (20a) and deployed (20b) in accordance with one embodiment of the present invention.

FIG. 21 shows a side view of the device shown in FIG. 1, having an inflated U-like shaped balloon in accordance with one embodiment of the present invention.

DETAILED DESCRIPTION OF THE INVENTION

Figure 1:
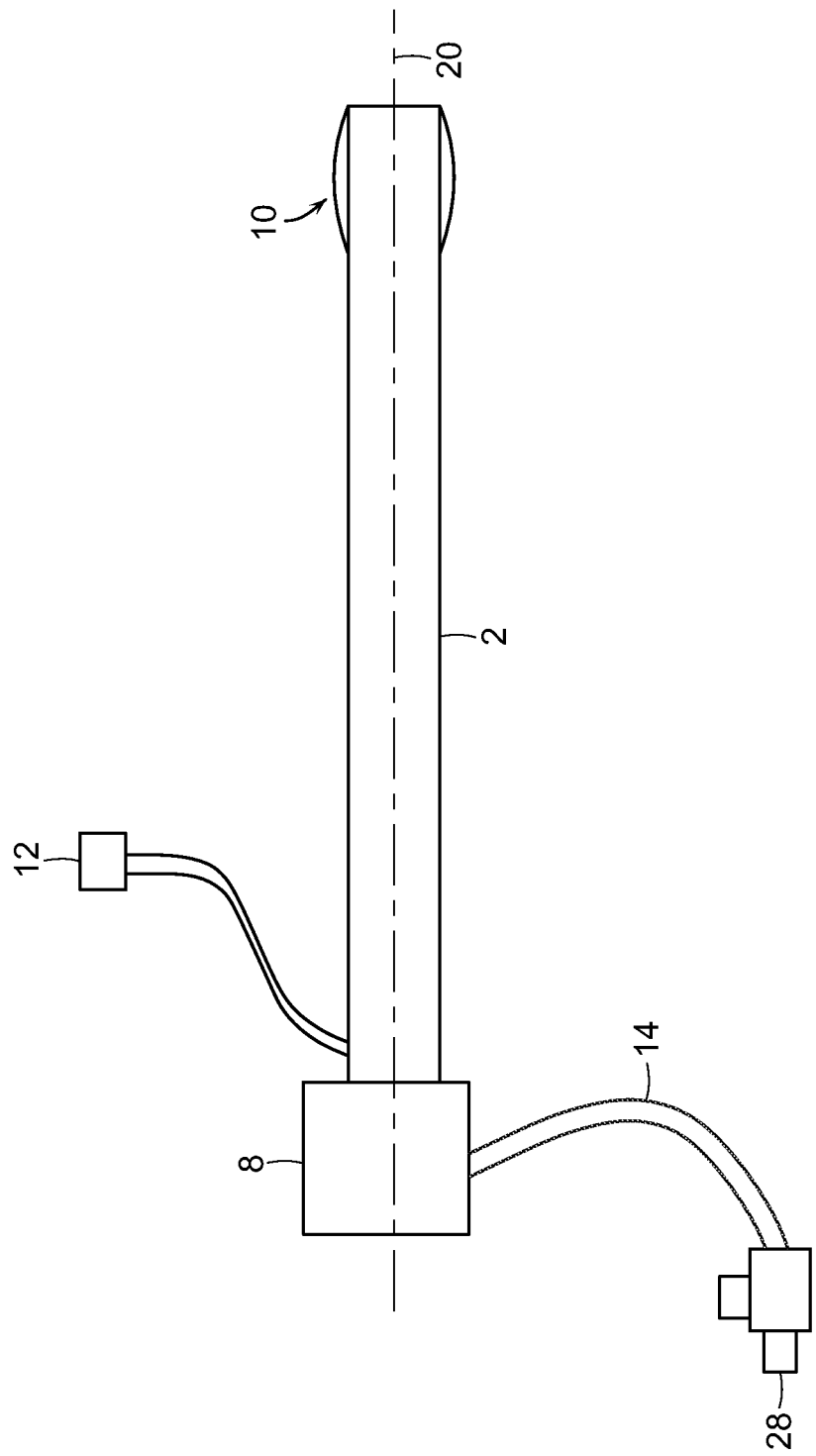
FIG. 1 shows a side view of a device for performing percutaneous and surgical interventions with a deflated balloon mechanism in accordance with one embodiment of the present invention.

The present invention provides methods and devices for performing percutaneous and surgical interventions. The device includes a mechanism near its distal end that prevents the device from pulling out of an anatomical structure, for example, a blood vessel during complex interventions.

In one preferred embodiment, the device is designed for performing a variety of vascular percutaneous interventions. For example, in one preferred embodiment, the device is in the form of a vascular sheath or a guide catheter and the mechanism near its distal end prevents the vascular sheath of guide catheter from pulling out of a blood vessel, for example, when switching from a retrograde to an antegrade approach and vice versa. The mechanism also allows the operator to use a single sheath when declotting AV hemodialysis fistulas. Further, the mechanism can serve as a lumen occluder while allowing large interventional devices to be passed through the sheath. This property, an embolic protection device, is particularly helpful during thrombectomy and vascular interventions.

Referring now to the various figures of the drawing, wherein like reference characters refer to like parts, there is shown various views of a device for performing percutaneous and surgical interventions 1, in accordance with the invention. The device is shown in the Figures and will be described below with particular reference to vascular sheaths. However, it is to be understood that the device is not limited to vascular sheaths and may include any type of devices for use in performing percutaneous and surgical interventions. For example, the device may also be in the form of a guide catheter. Devices for performing percutaneous and surgical interventions, including vascular sheaths and guide catheters, are well-known and, thus, although described and shown with reference to a preferred embodiment, the general features (e.g. size, shape, materials) of the a device for performing percutaneous and surgical interventions 1 may be in accordance with conventional devices for performing percutaneous and surgical interventions.

Figure 2:
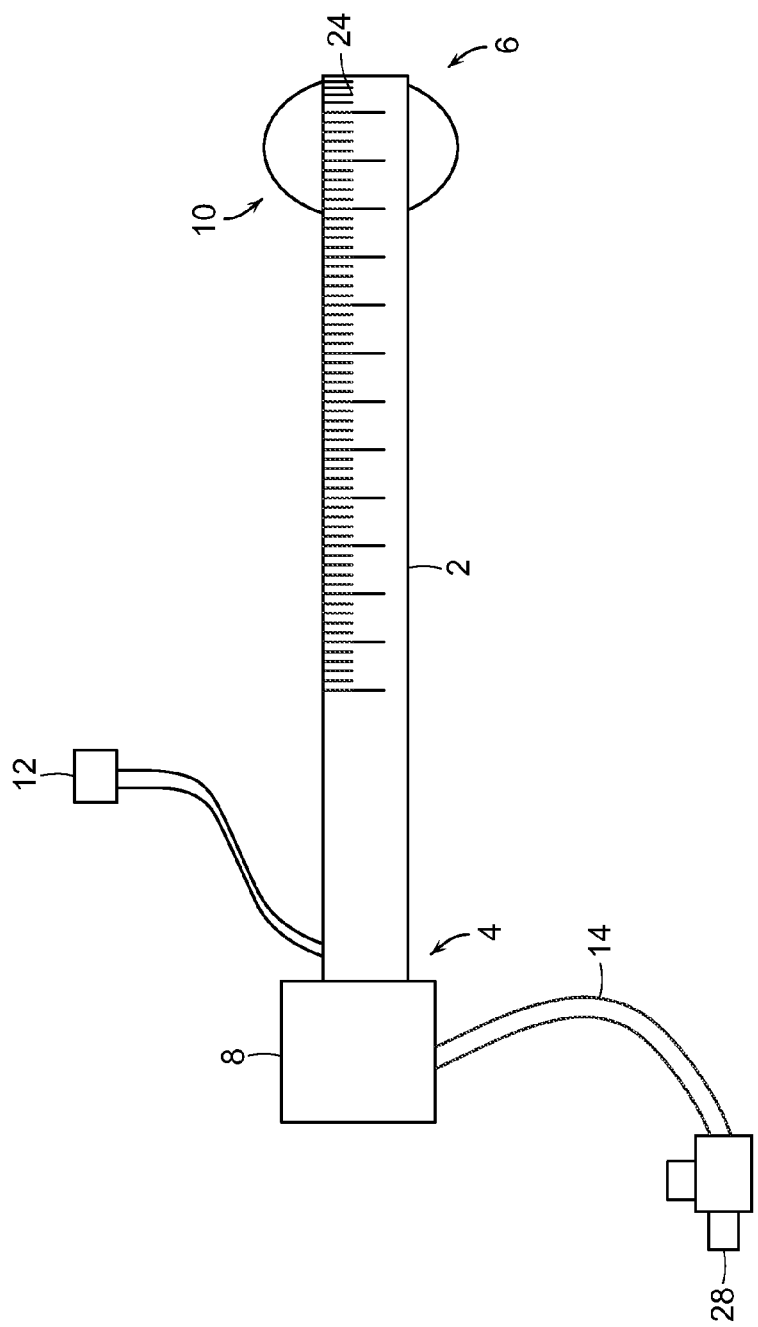
FIG. 2 shows a side view of the device shown in FIG. 1, having an inflated circular shaped balloon in accordance with one embodiment of the present invention.
Figure 3:
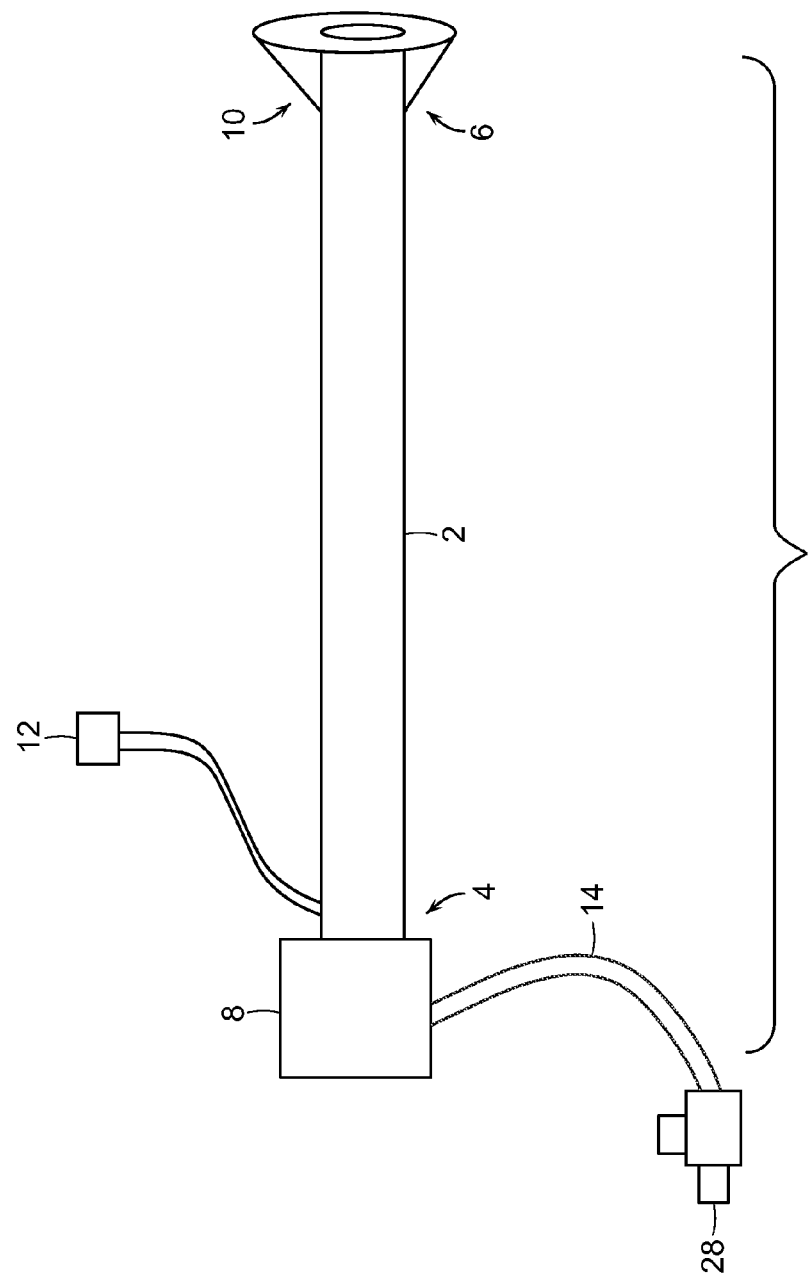
FIG. 3 shows a side view of the device shown in FIG. 1, having an inflated cone or funnel shaped balloon in accordance with another embodiment of the present invention.
Figure 4:
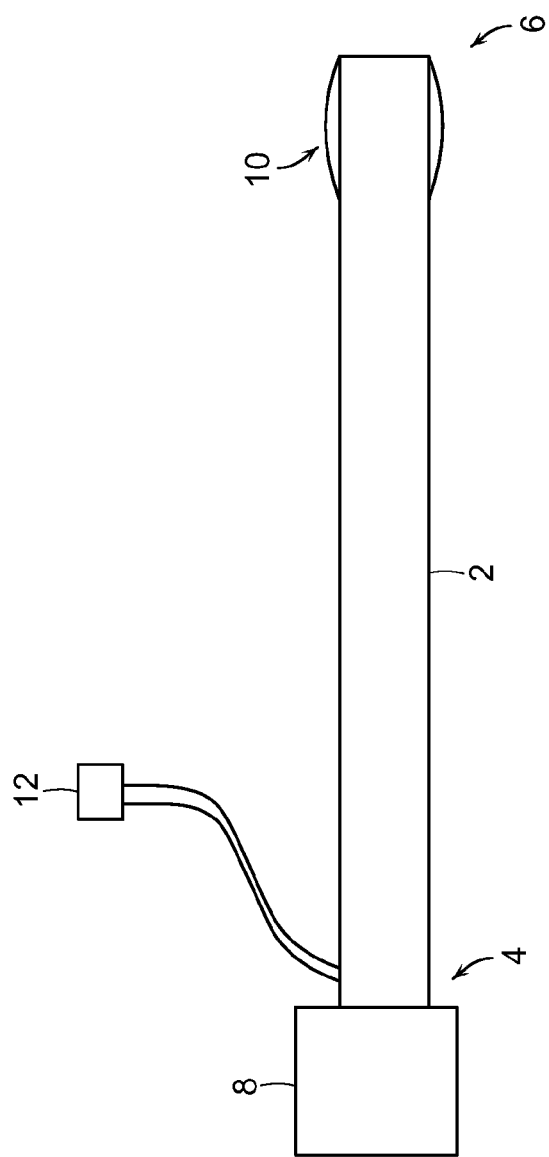
FIG. 4 shows a side view of a device for performing percutaneous and surgical interventions having a catheter hub at its proximal end and a deflated balloon mechanism in accordance with one embodiment of the present invention.

As shown in FIGS. 1-3, one embodiment of the vascular sheath 1 includes a tubular portion 2 having a proximal end 4 and a distal end 6. A lumen 3 extends from the proximal end 4 to the distal end 6 of the tubular portion 2. A hemostatic valve 8 is located at the proximal end 4 of the tubular portion 2 to prevent leakage of blood out of the sheath. A side-arm 14 in fluid communication with the lumen 3 may also be located near the proximal end 4 of the tubular portion 2.

Guide catheters are similar in general structure to vascular sheaths but typically do not include a hemostatic valve or a side arm. Further, guide catheters are not typically used in with a dilator. Generally, guide catheters are used in combination with vascular sheaths and are inserted through the lumen of a vascular sheath. Guide catheters are predominantly used in coronary interventions and can have a variety of shapes. Guide catheters are well known and, thus, the general features (e.g. size, shape, materials) of the vascular sheath 1 in the form of a guide catheter may be in accordance with conventional guide catheters. However, in some embodiments of the present invention, it may be desirable to provide a guide catheter having a hemostatic valve, side arm, and/or dilator and any combination of these additional elements.

As shown in the Figures, the tubular portion 2 of a device for performing percutaneous and surgical interventions has a generally cylindrical outer surface 18 and a longitudinal axis 20. The dimensions of the tubular portion 2 are not particularly limited and can vary depending on the ultimate use of the device. For example, when the device is a vascular sheath, in general, the tubular portion is sized such that it properly fits inside a desired blood vessel and provides access from the point of insertion to the area being treated. Further, when the vascular sheath is used as a conduit from the skin surface to the blood vessel to allow passages of catheters, guide wires, and instruments through vascular sheath 1, the tubular portion 2 is sized to allow these various instruments to be passed through the lumen 3.

Various instruments that are typically passed through the lumen 3 of the tubular portion 2 of a vascular sheath have a maximum diameter ranging from about 0.5 mm to about 10 mm and, thus, when the device is a vascular sheath used for passing various instruments through the tubular portion 2, the lumen 3 has a diameter of at least about 0.5 mm and, preferably, between about 1.35 mm and about 11 mm.

The outer diameter of the tubular portion 2 is not particularly limited and may be in accordance with tubular portions of conventional device for performing percutaneous and surgical interventions. Generally, the outer diameter of the tubular portion 2 of the device is limited only by the size of the anatomical structure that it is to be inserted in. The size of the tubular portion 2 of the device may also be limited based on the desired size of the incision through which the device is inserted and which must subsequently be sealed. For example, when the device is a vascular sheath, because the vascular sheath can be used on any blood vessels, the outer diameter can vary depending on the targeted blood vessel. In general, the tubular portion 2 preferably has an outer diameter that is smaller than the inner diameter of the blood vessel. The largest blood vessel(s) of the human body is the aorta, which has a diameter ranging from about 20 mm to about 70 mm. Thus, the largest outer diameter of the tubular portion 2 is preferably no greater than about 70 mm, preferably, no greater than about 10 mm, and more preferably, no greater than about 4.5 mm. The smallest blood vessel(s) of the human body are the coronary arteries, infrapopliteal arteries and intra-cranial arteries, which have a diameter ranging from about 1 mm to about 5 mm. Thus, for use on these small blood vessels, the outer diameter of the tubular portion 2 is preferably no greater than about 5 mm, more preferably, no greater than about 3 mm and, more preferably, no greater than about 1 mm. In general practice, it is preferable that the outer diameter of the tubular portion 2 is no greater than about 80% of the inner diameter of the blood vessel, more preferably, no greater than about 20%. However, while it is preferred that the outer diameter of the tubular portion 2 is no greater than the diameter of the blood vessel into which it is inserted, this is not necessary and, in some cases, the outer diameter of the tubular portion 2 is greater than the diameter of the blood vessel into which it is inserted.

In some embodiments, the diameter of the tubular portion 2 narrows at or near the distal end 6 along the mechanism that prevents the device from pulling out of the anatomical structure. Preferably, in this embodiment, the diameter of the tubular portion 2 at the distal end 6 along the mechanism that prevents the device from pulling out of the anatomical structure narrows such that the total diameter of the tubular portion 2 plus the mechanism in its non-deployed state is equal to or no greater than the greatest diameter of the tubular portion along the remainder of its length. This would ensure that when the device is placed into the anatomical structure, the mechanism would not overdilate the arteriotomy. Thus, for example, in one embodiment, wherein the mechanism is one or more balloons 10, the tubular portion 2 along the one or more deflated balloons 10 narrows such that the one or more balloons 10 can be deflated and compressed about the tubular portion 3 to form a total diameter of the tubular portion 2 plus deflated balloon(s) 10 that is equal to or no greater than the greatest diameter of the tubular portion 2 along the remainder of its length. Further, when the mechanism is one or more extensions 11, the extensions 11 can be retracted within the tubular portion 2 or can extend along the sides of the tubular portion 2 along the narrowed portion such that the total diameter of the tubular portion 2 plus retracted extensions 11 is equal to or no greater than the greatest diameter of the tubular portion 2 along the remainder of its length Thus, for example, if the mechanism is located at the distal end 6 of the tubular portion 2, the tubular portion 2 may taper toward the distal end as shown in FIG. 19a-b. If the mechanism is located somewhere between the proximal end 4 and the distal end 6 of the tubular portion 2, the tubular portion 2 may narrow at the location of the mechanism, for example, in an hour-glass-like shape as shown in FIG. 20a-b.

The length of the tubular portion 2 is not particularly limited and may be in accordance with tubular portions of conventional devices for performing percutaneous and surgical interventions. Generally, the lengths of the tubular portions may vary depending on the use of the device, the insertion point of the tubular portion and the distance to the target area in the anatomical structure. Further, when the device is used as a conduit through which other interventional devices may be passed, it is often desirable to form the tubular portion 2 so that it is long enough to fully accommodate the longest interventional device that will be inserted. For example, in one embodiment the device is a vascular sheath 1 designed for use in a variety of cardiac procedures, including procedures within the coronary arteries. The vascular sheath 1, when used during cardiac procedures, can be inserted through a blood vessel in the upper thigh or, alternatively, can be inserted through a blood vessel in the arm. For example, in one preferred embodiment, the vascular sheath 1 is inserted by anesthetizing an area the patient's upper thigh and inserting the vascular sheath 1 through a blood vessel in the upper thigh and towards the heart. As such, the vascular sheath 1 preferably has a length ranging from about 5 cm to about 100 cm, more preferably, from about 5 cm to about 30 cm. The longest interventional devices typically have a length that ranges from about 30 cm to about 135 cm and, thus, such lengths of tubular portions 2 will accommodate a variety of interventional devices. Of course, the length of the vascular sheath 2 may vary depending on the point of insertion, the distance from the point of insertion to the target site and the types of interventional devices that will be used in each procedure.

In some embodiments, as shown in FIG. 2, the tubular portion 2 includes indicia 24 along its length to indicate the depth of insertion of the tubular portion 2.

Materials for fabricating the tubular portion 2 of the devices for performing percutaneous and surgical interventions. are well-known and include, by way of example TEFLON, polyethylenes, polyamide elastomers, polyurethanes, nylons including polyamide homopolymers and polyamide copolymers. Because the tubular portion 2 enters the body and anatomical structures, the materials used in fabricating the tubular portion 2 are biocompatible. Preferably, the tubular portion 2 is somewhat flexible along its length to allow bending and maneuvering of the tubular portion 2 as it passes within an anatomical structure, such as a blood vessel. In addition, the tubular portion 2 preferably is sufficiently stiff to resist kinking, which could damage interventional devices and stents passed through the lumen 3 of the tubular portion 2. Preferably, at least the distal end 6 of the tubular portion has adequate rigidity to allow puncture and entry through the wall of an anatomical structure. The tubular portion 2 may be designed with a rigid distal end 6 and flexibility along its length by, for example, fabricating the distal end 6 of the tubular portion 2 of a material more rigid than the material used to form the length of the tubular portion 2. Such materials may be readily determined by one of skill in the art. Alternatively, the entire tubular portion 2, including the distal end 6, may be fabricated of the same somewhat flexible material and the walls of the tubular portion 2 may be formed thicker at the distal end 6 or, for example, the walls of the distal end 6 may be reinforced. In some embodiments, the distal end 6 is pointed or beveled to enhance puncturing ability of the tubular portion 2.

Figure 22:
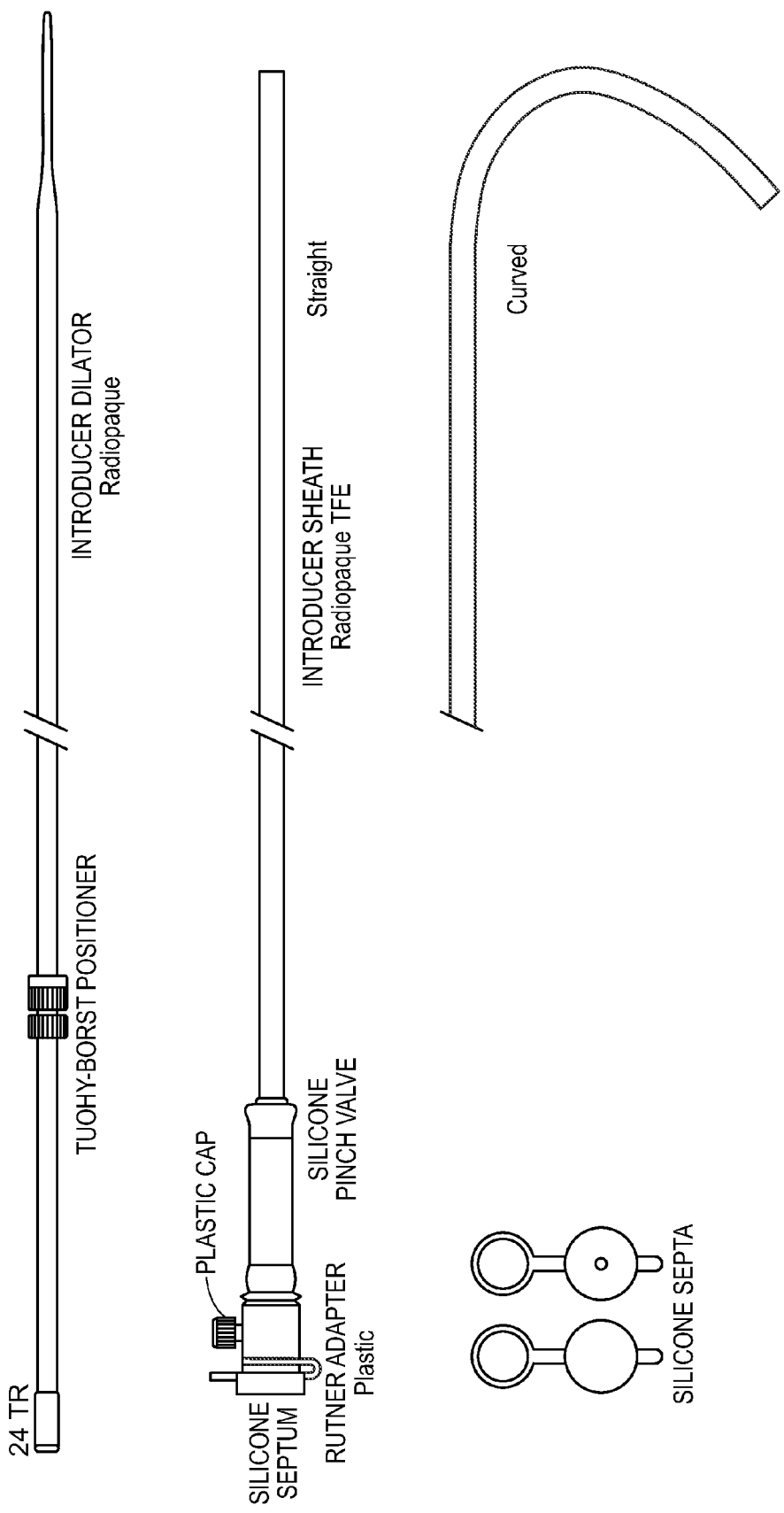
FIG. 22 shows an exploded view of a silicone pinch valve assembly.

A silicone pinch valve 40, shown in FIG. 22, may further be included in some embodiments of the present invention. As shown, the silicone pinch valve 40 is preferably located near the proximal end 4 of the tubular portion 2, preferably at the proximal end 4 of the tubular portion 2. In some embodiments, the silicone pinch valve 40 replaces the hemostatic valve 8 at the proximal end 4 of the tubular portion 2. Thus, the vascular sheath 1 may include a removable hemostatic valve 8 that can be removed and replaced with the silicone pinch valve 40 if desired. The silicone pinch valve 40 could be removably mountable on the tubular portion 2 using, for example, mating threaded portions on the silicone pinch valve 40 and the tubular portion 2. The silicone pinch valve 40 may also be designed to snap onto and off of the end of the tubular portion 2. The silicone pinch valve 40 assists in controlling backbleeding while the vascular sheath 1 is inserted and during manipulation of the vascular sheath 1. The silicone pinch valve 40 preferably includes a cap 42, preferably fabricated of a plastic, that functions like a side arm, allowing aspiration and injection of materials through the tubular portion 2. In some embodiments, the plastic cap 42 could be replaced with a side arm. The silicone pinch valve 40 may also include a Rutner adapter 44 and a silicone septum 46, which function as a hemostatic valve. The Rutner adapter 44 is preferably rigid and fits into the soft silicone pinch valve 40. The silicone septum 46 fits on the end of the Rutner adapter 44. In some embodiments, a central hole (not shown) is located in the silicone septum 46 through which small catheters may be introduced. In embodiments where a large device is introduced through the tubular portion or clot removed from a blood vessel, the silicone septum is preferably opened or removed to provide a large aperature that is at least as large as the diameter of the Rutner adapter 44 and lumen 3.

In some embodiments, the silicone pinch valve 40 is positioned between the hemostatic valve 8 and the tubular portion 2 In this embodiment, the hemostatic valve 8 may be directly connected to the silicone pinch valve 40 or, for example, indirectly connected to the silicone pinch valve 40. For example, the silicone pinch valve 40 could be located interposed with portions of tubular portion 2 on either side and the hemostatic valve 8 at the proximal end. The hemostatic valve 8 may or may not be removable or could be of the configuration of the Rutner adapter 44 and silicone septum 46.

Located near the distal end 4 of the tubular portion 2 is a mechanism that prevents the device 1 from pulling out of an anatomical structure during complex interventions. Of course, the location of the mechanism is not particularly limited and may also be located elsewhere along the length of the tubular portion 2. For example, in one embodiment, the device is a vascular sheath or a guide catheter and the mechanism prevents the vascular sheath or guide catheter from pulling out of a blood vessel when switching from an antegrade to a retrograde approach and vice versa.

In one embodiment, as shown in FIGS. 1-5, the mechanism is in the form of an inflatable balloon 10 located at the distal end 6 of the tubular portion 2. The inflated balloon 10 is preferably coaxial with the longitudinal axis 20 of the tubular portion 2. The balloon 10 can be fabricated of any expandable or non-expandable materials that are biocompatible. Preferably, the balloon 10 is fabricated of a material that expands away from the tubular portion 2 when inflated such that the distal end 6 of the tubular portion 2 becomes larger in cross section on account of the inflated balloon 10. Preferably, the balloon 10 is fabricated of a material that compresses about the tubular portion 2 when deflated such that the balloon 10, when deflated, does not significantly increase the diameter of the distal end 6 of the tubular portion 2 when the sheath is inserted and withdrawn. When used herein, "does not significantly increase the diameter of the tubular portion" means that, when the device is placed into the anatomical structure, the mechanism would not overdilate the arteriotomy.

Suitable materials for use in forming the balloon 10 are well known in the art and include, by way of example, PET, polyurethane, polyolefin, polyvinylchloride, any materials used to form angioplasty type balloons, and materials used in forming balloons used in the Swan Ganz catheter or the Fogarty balloon catheter.

As shown, the balloon 10 is preferably attached directly to the distal end 6 of the tubular portion 2. Of course, the balloon 10 may also be located elsewhere along the length of the tubular portion 2. Preferably, the balloon 10 is compressed about the diameter of the tubular portion 2 for insertion and withdrawal of the vascular sheath 1 into and out of the body.

Preferably, the balloon 10 is inflatable to different sizes to enable use of the vascular sheath 1 in various procedures. For example, when the vascular sheath 1 is used in a procedure requiring repositioning the vascular sheath from a retrograde to an antegrade position in a blood vessel, and vice versa, the balloon 10 is inflated so that it is smaller than the inner diameter of the blood vessel and larger than the arteriotomy through which the vascular sheath 1 entered the blood vessel. By sizing the balloon 10 larger than the arteriotomy through which the vascular sheath 1 entered the blood vessel, the tubular portion 2 is prevented from completely exiting from the blood vessel during manipulation from a retrograde to an antegrade position, and vice versa. The vascular sheath 1 can also be used to aspirate blood clots, emboli and other materials from the blood vessel. When used in this way, the balloon 10 is inflated until it obstructs the blood vessel. In such a procedure, the vascular sheath 1 is inserted into the blood vessel with the distal end 6 of the tubular portion 2 facing towards the material to be aspirated. If the material, for example, a blood clot, has lodged in the blood vessel, antegrade flow will apply a pressure head to keep this clot lodged in its position. The balloon 10 is then inflated until it occludes the blood vessel, thereby blocking blood flow through the blood vessel. Back-bleeding will then cause the blood clot to propagate towards the vascular sheath 1. An aspiration device connected to the side arm 14 of vascular sheath 1 can then be used to aspirate the blood clot out of the blood vessel through the lumen 3. Thus, the vascular sheath 1 could be inserted into the blood vessel in a retrograde position, the balloon inflated to occlude the blood vessel and blood clots, emboli and other materials could be aspirated from one side of the blood vessel, followed by partial deflation of the balloon 10, repositioning of the vascular sheath 1 to an antegrade position, re-inflation of the balloon 10 to occlude the blood vessel, and aspiration of and blood clots, emboli and other materials on the other side of the blood vessel.

Figure 5:
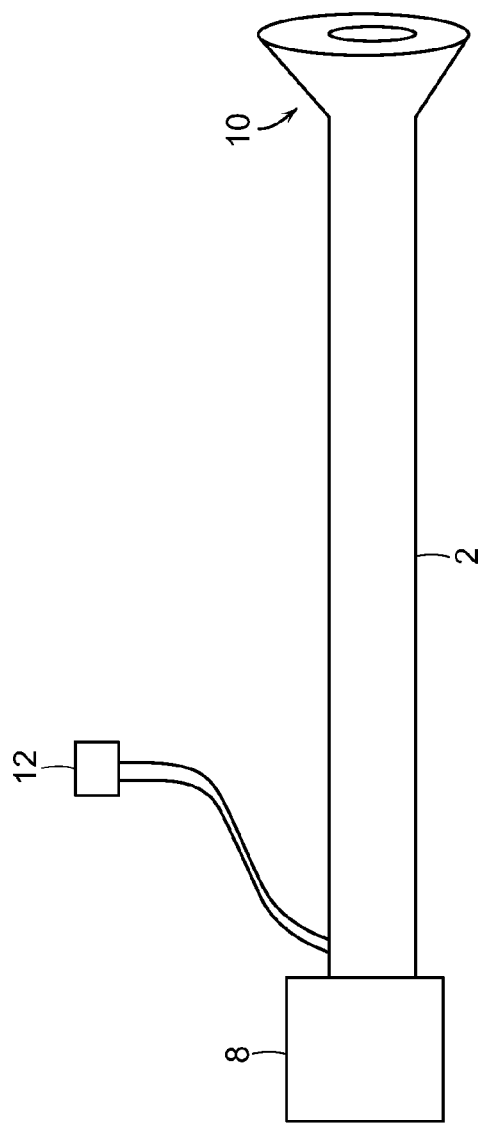
FIG. 5 shows a side view of the device in FIG. 4, having an inflated cone or funnel shaped balloon in accordance with one embodiment of the present invention.
Figure 6:
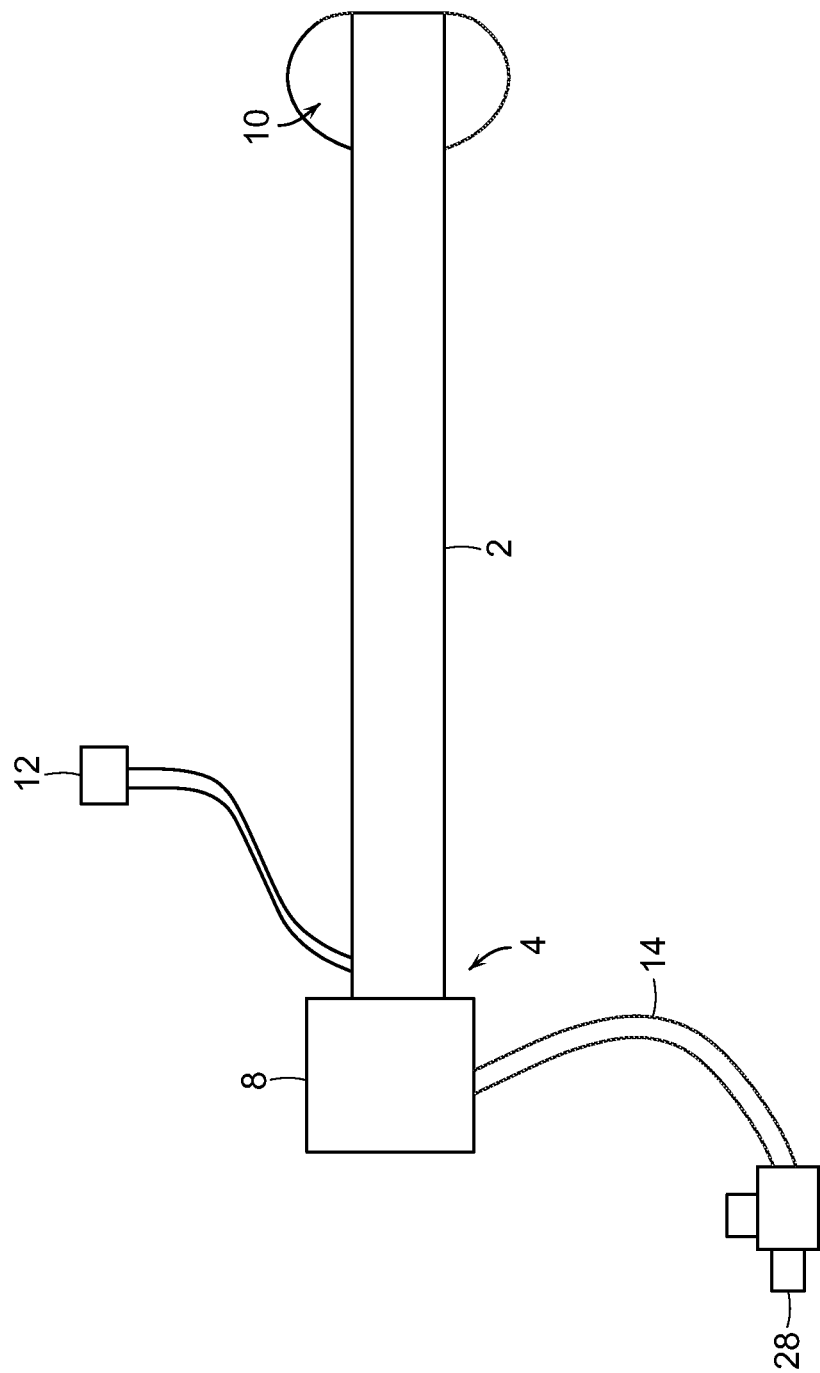
FIG. 6 shows a side view of a device for performing percutaneous and surgical interventions having a catheter hub at its proximal end and an inflated balloon mechanism flush with the distal end of the tubular portion in accordance with one embodiment of the present invention.
Figure 7:
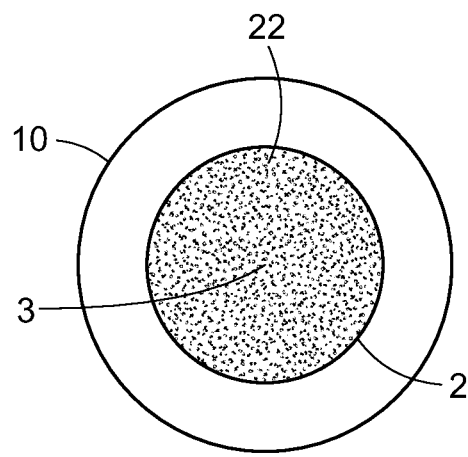
FIG. 7 shows a front view of a device for performing percutaneous and surgical interventions having an inflated balloon and a single balloon inflation aperture in accordance with one embodiment of the present invention.

When the vascular sheath is used to aspirate materials out of the blood vessel, it is preferable to form the vascular sheath 1 and balloon 10 in a manner that will prevent the emboli, blood clots and other materials from being lodged between the balloon 10 and the distal end 6 of the tubular portion 2. For example, in one embodiment, the vascular sheath 1 and balloon 10 are formed so that the balloon 10 is flush with the distal end 6 of the tubular portion 2, as shown in FIGS. 3 and 5. In another embodiment, the vascular sheath 1 and balloon 10 are formed so that the balloon 10 extends beyond the distal end 6 of the tubular portion 2. In yet another embodiment, the vascular sheath 1 and balloon 10 are formed so that the balloon 10 extends behind the distal end 6 of the tubular portion 2. In one embodiment, as shown in FIG. 6, the balloon 10 is in the form of a round or oval shaped balloon that, when inflated, expands flush with the distal end 6 of the tubular portion 10. In another embodiment, as shown in FIGS. 3 and 5, the balloon 10 is funnel-like or cone-like in shape, wherein the large end of the funnel or cone is at the distal end 6 of the tubular portion 2 and inflates perpendicular and flush with the distal end 6 of the tubular portion 2. The funnel can also protrude out in front of distal end 6, to create a true "funnel" appearance of the balloon and distal tip. Still further, the funnel can also extend so that it is behind the front of distal end 6. In another embodiment, the balloon 10 is U-like in shape, as shown in FIGS. 21*a-c*. The U-shaped balloon 10 can protrude out in front of the distal end 6 of the tubular portion 2, as shown on FIG. 21*a*, can extend behind the distal end 6 of the tubular portion 2, as shown on FIG. 21*b* or can extend flush with the distal end 6 of the tubular portion 2, as shown on FIG. 21*c*. These embodiments will provide complete aspiration of the emboli, blood clots and other materials from the blood vessel.

When the vascular sheath 1 is used to insert a stent or perform angioplasty, the balloon 10 is also preferably inflated until it obstructs the vessel. A wire (not shown) is used to cross through the obstruction. Then the stent (not shown) is deployed or angioplasty performed, thus opening the blood vessel. During the manipulation of the wire and stent, it is possible to withdraw blood, blood clots, and debris by aspiration through side arm 14. Alternatively, the aspiration can take place after the stent has been deployed. This would be determined by the location of the sheath relative to the lesion (i.e. upstream vs. downstream).

The size of the balloon 10 is not particularly limited. For example, when the device is used within a blood vessel, the inflated cross section of the balloon 10, as measured perpendicular to the length of the tubular portion, can range from its deflated size to as large as, or larger than, the inner diameter of the blood vessel. When used on other anatomical structures, the inflated cross section of the balloon 10 may vary and is limited only by the size of the anatomical structure and the particular requirements of the procedure. Preferably, so that the device can be used for various procedures requiring various inflation sizes, the balloon 10 is inflatable to any size in between its deflated size and its maximum inflated size by simply controlling the amount of air or material injected into the balloon 10. The length of the balloon, as measured parallel to the length of the tubular portion 2 is not limited and, for example, when the device is used in blood vessels, is preferably no greater than three quarters the length of the tubular portion 2, more preferably, between about 1 mm and about 150 mm, more preferably, between about 3 mm and about 40 mm.

Inflation of the balloon 10 is accomplished through an inflation port 12. In a preferred embodiment, as shown in FIGS. 7-10, the wall of the tubular portion, which extends from the inner diameter of the tubular portion to the outer diameter of the tubular portion, has embedded inside one or more inflation channels 22 that connect the inflation port 12 to the balloon 10. In a preferred embodiment, the balloon 10 is mounted over a portion of the distal end 6 of the tubular portion 2. The one or more channels 22 extend from the balloon inflation port 12 to a point on the tubular portion 2 covered by the balloon 10. One or more apertures 30 are located along the length of the tubular portion 2 covered by the balloon 10 such that air or other material inserted through inflation port 12 passes through the one or more channel 22, through the one or more apertures 30 and into the balloon 10.

Figure 8:
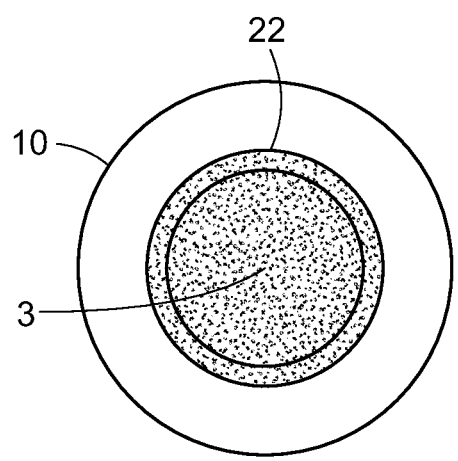
FIG. 8 shows a front view of a device for performing percutaneous and surgical interventions having an inflated balloon and an open circular strip for balloon inflation in accordance with another embodiment of the present invention.
Figure 9:
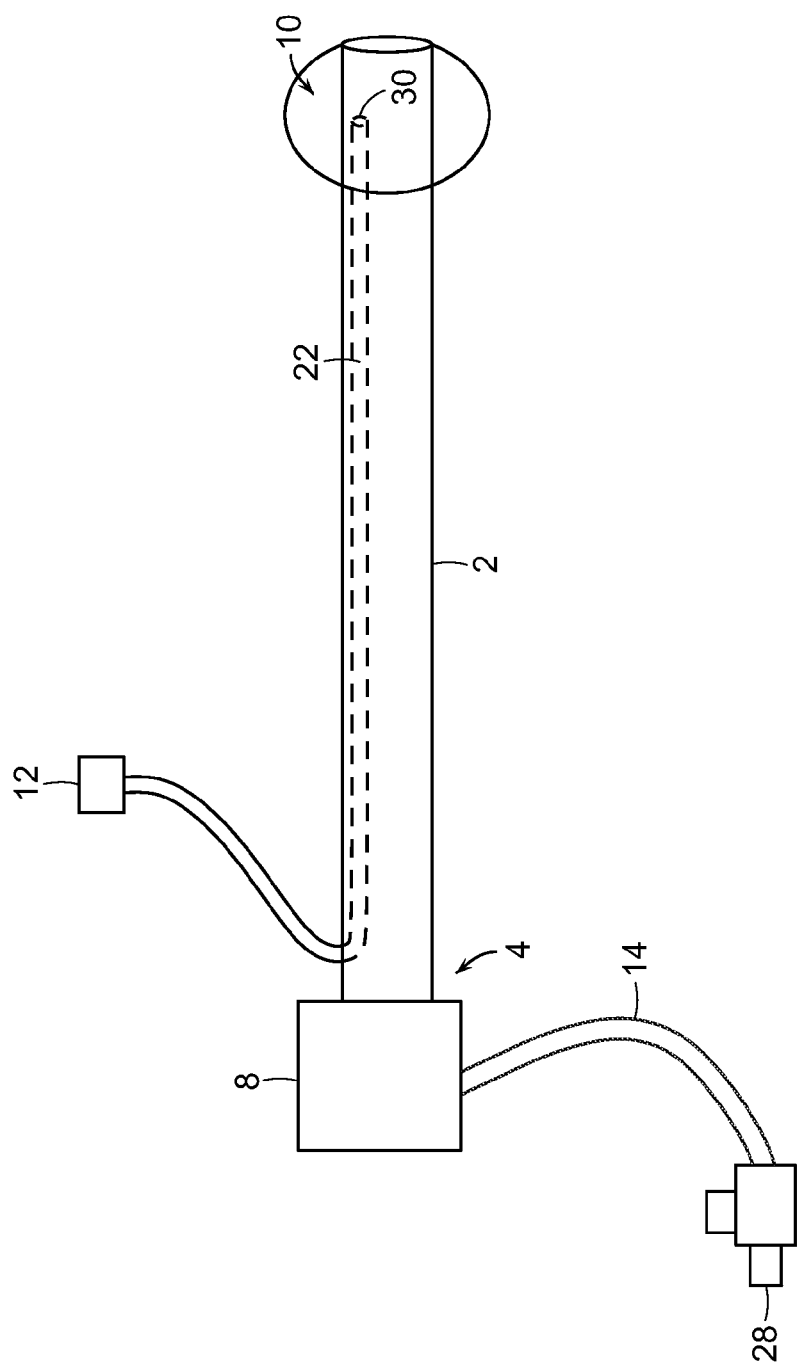
FIG. 9 shows a side view of the device of FIG. 7 showing a single balloon inflation channel and aperture.
Figure 10:
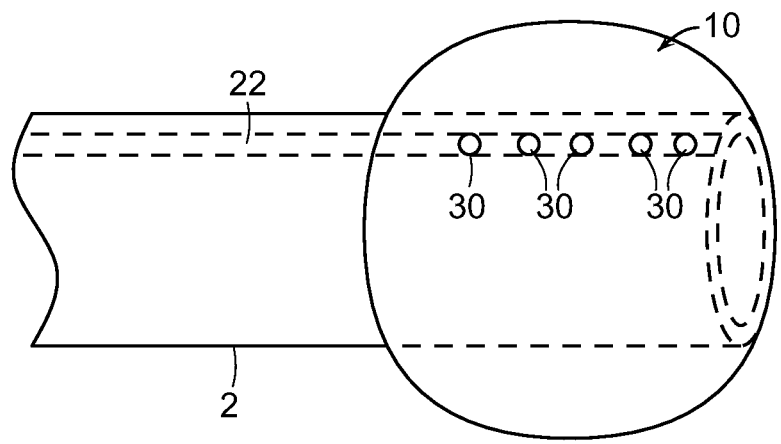
FIG. 10 shows a side view of a device for performing percutaneous and surgical interventions having an inflated balloon, a single balloon inflation channel and a plurality of balloon inflation apertures.
Figure 11:
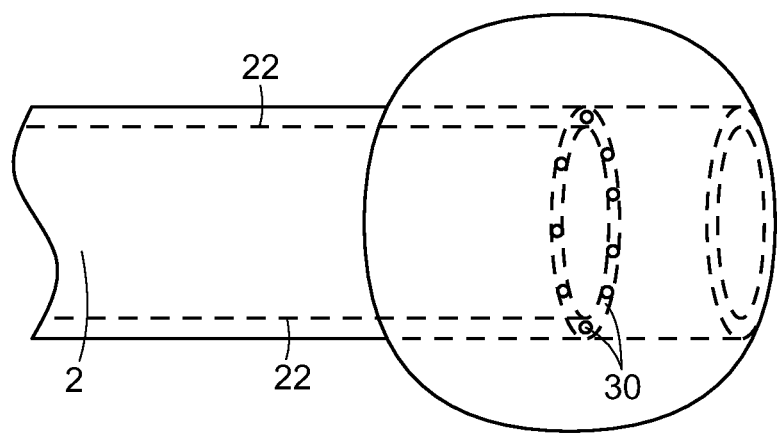
FIG. 11 shows a shows a side view of a device for performing percutaneous and surgical interventions having an inflated balloon, a plurality of balloon inflation channels and a plurality of balloon inflation apertures.

In one embodiment, as shown in FIGS. 9 and 10, a single tubular inflation channel 22 connects the inflation port 12 to the balloon. In this embodiment, one or more apertures 30 may be located in the tubular portion 2 covered by the balloon 10 in the pathway of the inflation channel 22. In another embodiment, as shown in FIG. 8, the wall of the tubular portion 2 can be hollow along its circumference between the inner diameter and the outer diameter of the tubular portion 2, and the channel 22 comprises the hollow portion. As shown in FIG. 11, one or more apertures 30 may be located along the circumference of the tubular portion 2 in the portion covered by the balloon 10. Alternatively, an open circular strip 32 may be formed along the circumference of the tubular portion 2 covered by the balloon 10 for conveying the air or other balloon inflation materials from the channel 22 into the balloon 10.

Figure 12:
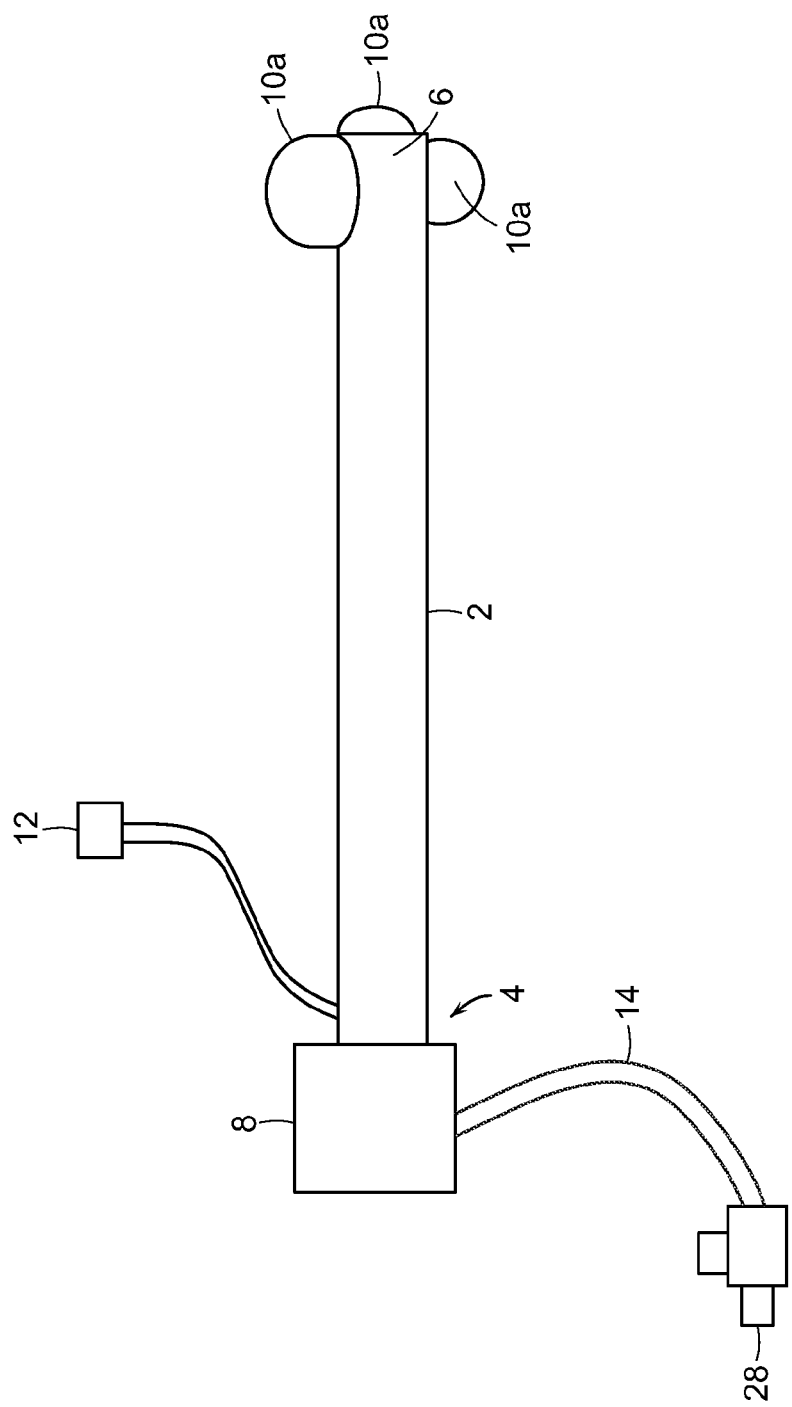
FIG. 12 shows a shows a side view of a device for performing percutaneous and surgical interventions having a plurality of inflatable balloons near the distal end of the tubular portion.

In another embodiment, as shown in FIG. 12, the mechanism that prevents the device from pulling out of an anatomical structure during complex interventions, e.g. when switching from an antegrade to a retrograde approach in a blood vessel and vice versa, comprises a plurality of balloons 10a located near the distal end 6 of the tubular portion 2. The plurality of balloons 10a are preferably located about the outer circumference of the tubular portion 2. The fabrication and design of the plurality of balloons 10a are similar to the fabrication and design of the single balloon 10 described above. For example, the materials used on fabricating the plurality of balloons 10a are the same as those used in fabricating the single balloon 10. The balloons 10a are preferably compressed to the diameter of the tubular portion 2 for insertion and withdrawal of the vascular sheath 1. Further, the balloons 10a are preferably inflatable to different sizes to enable use of the device in various procedures. For example, when the device is used in a blood vessel, the balloons 10a are preferably inflatable to a size wherein the cross section of the tubular portion 2 plus balloons 10a is larger than the arteriotomy and to a size wherein the balloons 10a obstruct the blood vessel.

The balloons 10a can also come in a variety of shapes. For example, each of the balloons 10a may inflate to a circular or oval shape. In another embodiment, the plurality of balloons 10a may inflate such that the plurality of balloons 10a together form a ring about the distal end 6 of the tubular portion 2. In some embodiments, the ring inflates flush with the distal end 6 of the tubular portion 2. In another embodiment, the plurality of balloons 10a inflate such that, when inflated, the plurality of balloons 10a together form a funnel-like shape. In some embodiments, the funnel-like shape may inflate flush with the distal end 6 of the tubular portion 2. In other embodiments, the funnel can also protrude out in front of distal end 6, to create a true "funnel" appearance of the balloon and distal end of the tubular portion.

Figure 13:
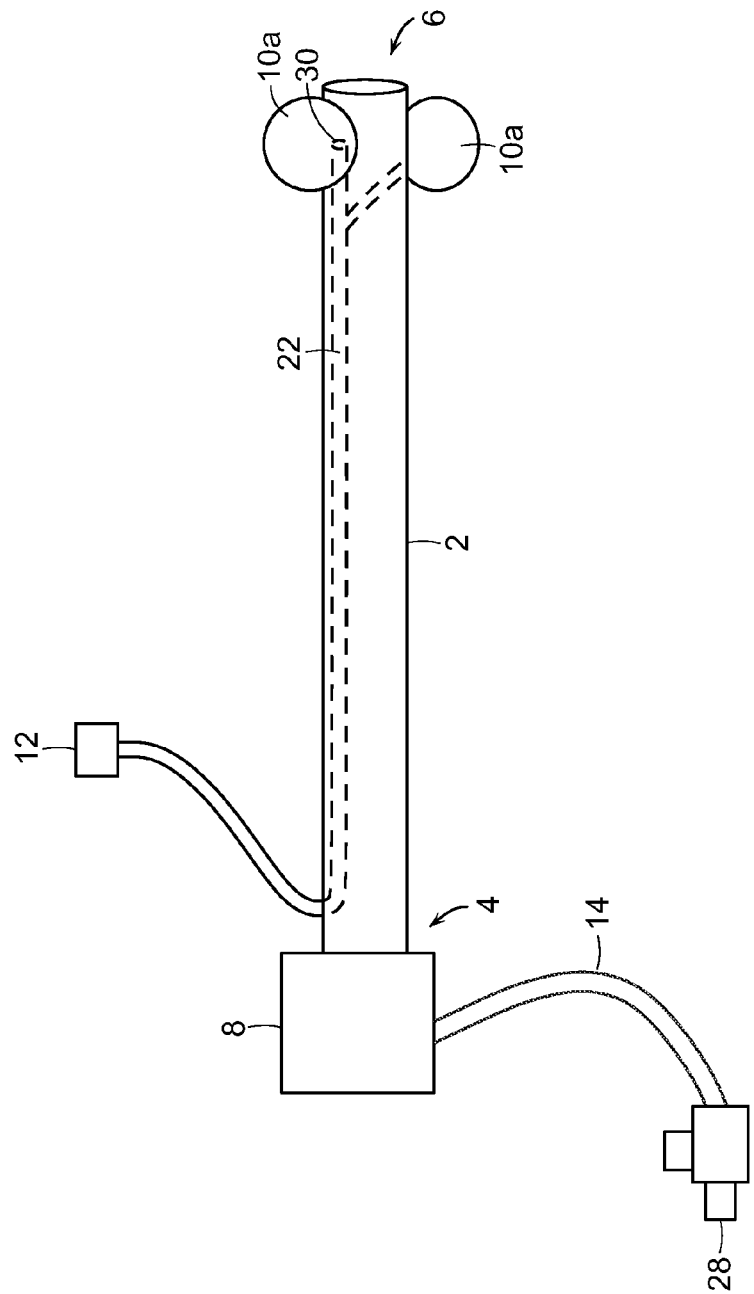
FIG. 13 shows a shows a side view of a device for performing percutaneous and surgical interventions having a plurality of inflatable balloons near the distal end of the tubular portion and a single balloon inflation channel that splits to provide inflation to each of the balloons.
Figure 14:
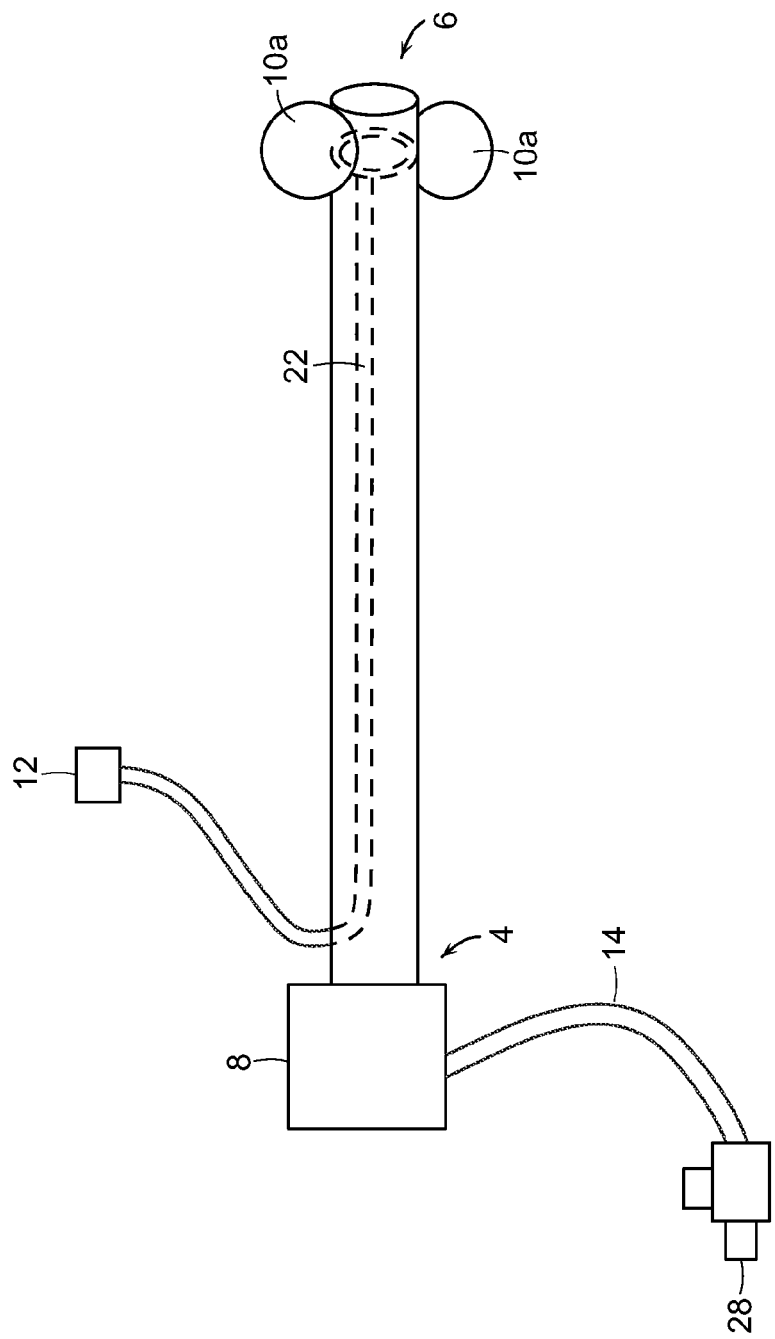
FIG. 14 shows a shows a side view of a device for performing percutaneous and surgical interventions having a plurality of inflatable balloons near the distal end of the tubular portion and a single balloon inflation channel that extends to a ring that provides inflation to each of the balloons.

For the plurality of balloons 10a, there may be a single inflation port 12 in fluid communication with all of the balloons 10a or multiple inflation ports 12a in fluid communication each of the balloons 10a. One or more inflation channels 22a embedded inside the tubular portion 2 preferably connect the inflation port(s) 12a to the balloons 10a. In one embodiment, a single inflation channel 22 extends from an inflation port 22 and splits to extend to each of the balloons 10a, as shown in FIG. 13. Alternatively, the single inflation channel 22 can extend towards the balloons 10a and extend within the circumference of the tubular portion 2 to each balloon 10a as shown in FIG. 14. In another embodiment, a plurality of inflation ports 12a and inflation channels 22a can be formed in the tubular portion 2, for example, each extending to a separate balloon 10a.

Figure 15:
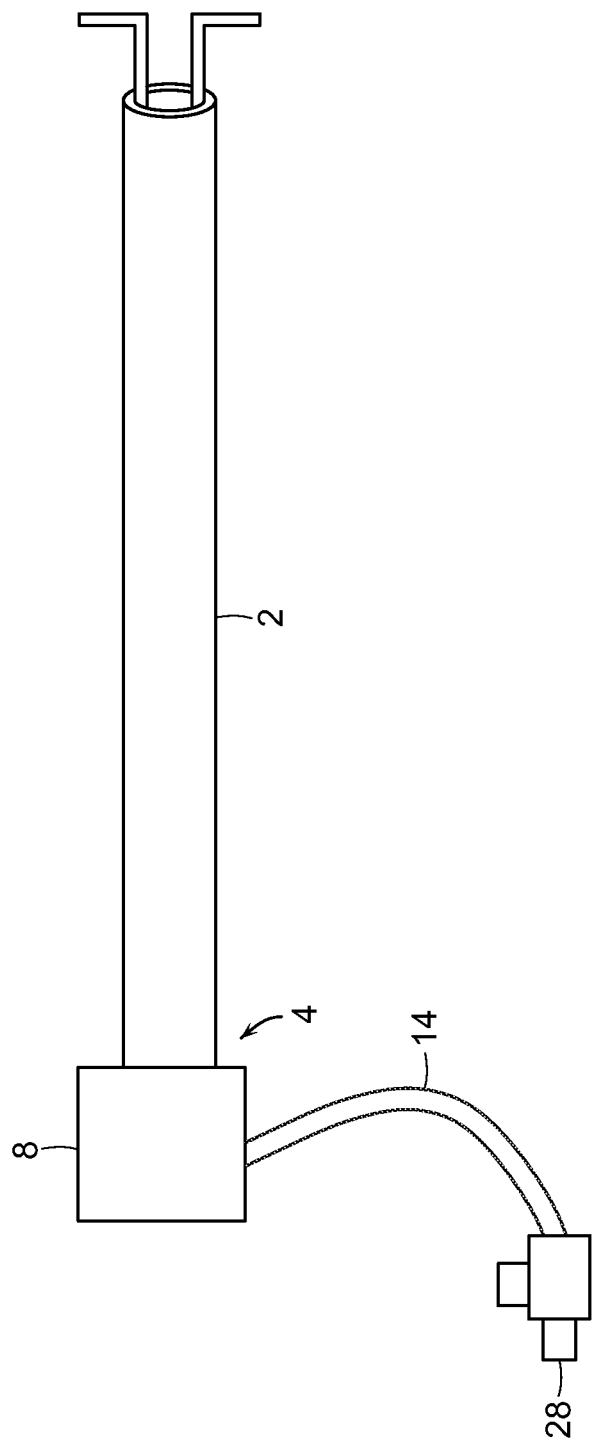
FIG. 15 shows a side view of a device for performing percutaneous and surgical interventions having a plurality of deployable extensions extending from the distal end of the device in accordance with one embodiment of the present invention.
Figure 16:
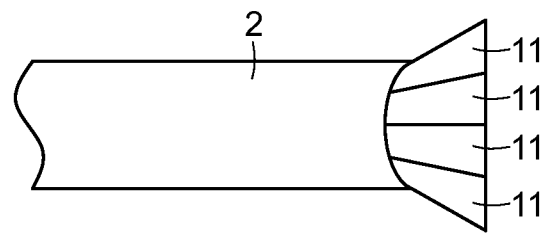
FIG. 16 shows a side view of the distal end of a device for performing percutaneous and surgical interventions having a plurality of extensions extending in a funnel-like shape from the distal end of the device in accordance with one embodiment of the present invention.
Figure 17:
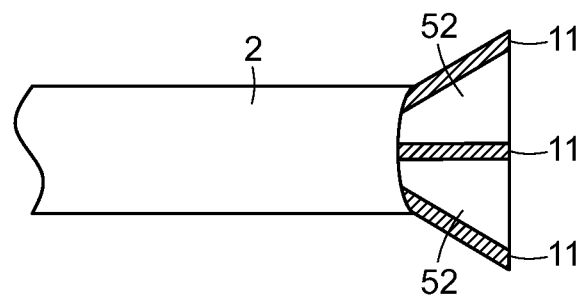
FIG. 17 shows a side view of the distal end of a device for performing percutaneous and surgical interventions having a plurality of extensions, with a material connecting the extensions together, extending in a funnel-like shape from the distal end of the device in accordance with another embodiment of the present invention.
Figure 18:
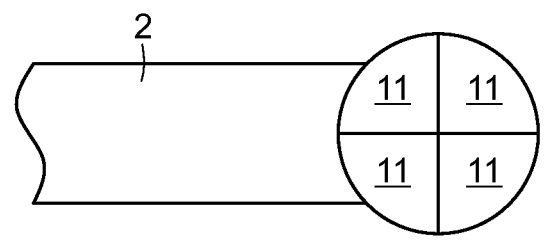
FIG. 18 shows a side view of the distal end of a device for performing percutaneous and surgical interventions having a plurality of extensions extending in a circular-like shape from the distal end of the device in accordance with one embodiment of the present invention.

In another embodiment, as shown in FIGS. 15-18, the mechanism that prevents the device from pulling out of an anatomical structure is in the form of one or more extensions 11 near the distal end 6 of the tubular portion 2. For example, two or more arm-like extensions 11 can be located near the distal end 6 of the tubular portion 2, as shown in FIG. 15. In another embodiment, one or more extensions 11 forming a funnel-like shape are located near the distal end 6 of the tubular portion 2, as shown in FIGS. 16 and 17. For example, as shown in FIG. 16, a plurality of extensions 11 may deploy to connect together and form a funnel shape. In another embodiment, a plurality of extensions 11 may deploy with a material 52 connecting the extensions 11 together, like an umbrella, to form a funnel shape, as shown in FIG. 17. Any type of biocompatible material may be used to connect the extensions. In yet another embodiment, one or more extensions 11 forming a circular shape are located near the distal end 6 of the tubular portion 2, as shown in FIG. 18. As with the funnel shape, the plurality of extensions 11 may deploy to connect together and form a circular shape or, for example, the plurality of extensions 11 may deploy with a material 52 connecting the extensions 11 together to form a circular shape.

These extensions 11 are preferably retractable to allow for retraction and deployment of the extensions 11 during use of the device. A deployment/retraction mechanism (not shown) is preferably located near the proximal end of the device so that a user of the device can remotely retract and deploy the extensions 11 during use. Preferably, the extensions 11 would be deployable by the user of the device such that, during insertion and withdrawal of the device into and out of the anatomical structure, the extensions 11 would be in their refracted state and the cross section of the tubular portion 2 as the device is inserted and withdrawn is not increased or not significantly increased by the extensions. For example, the extensions could be housed within the tubular portion 2 or, for example, folded back against the side surfaces of the tubular portion 2 during insertion of the device into the anatomical structure. Upon insertion of the device into the anatomical structure to the desired site, the extensions 11 could them be deployed by the user using the deployment/retraction mechanism. Prior to withdrawal of the device from the anatomical structure, the extensions 11 would be returned to their retracted state using the deployment/retraction mechanism.

In some embodiments, the extensions 11 are deployable to different sizes to enable use of the devices in various procedures. For example, when the device is a vascular sheath used in a procedure requiring repositioning the vascular sheath from a retrograde to an antegrade position, and vice versa, the extensions 11 are deployed so that the cross section of the tubular portion 2 plus extensions 11 is smaller than the inner diameter of the blood vessel and larger than the arteriotomy through which the vascular sheath 1 entered the blood vessel. By sizing the extensions 11 so that the cross section of the tubular portion 2 plus extensions 11 is larger than the arteriotomy through which the vascular sheath 1 entered the blood vessel, the tubular portion 2 is prevented from completely exiting from the blood vessel during manipulation from a retrograde to an antegrade position and vice versa.

In some embodiments, the vascular sheath 1 is used to aspirate blood clots, emboli and other materials from the blood vessel. When used in this way, the extensions 11 are designed such that when fully deployed, the blood vessel is obstructed. In such a procedure, the vascular sheath 1 is inserted into the blood vessel with the distal end 6 of the tubular portion 2 facing towards the material to be aspirated. If the material, for example, a blood clot, has lodged in the blood vessel, antegrade flow will apply a pressure head to keep this clot lodged in its position. The extensions 11 are then deployed until they occlude the blood vessel, thereby blocking blood flow through the blood vessel. Back-bleeding will then cause the blood clot to propagate towards the vascular sheath 1. An aspiration device connected to the side arm 14 of vascular sheath 1 can then be used to aspirate the blood clot out of the blood vessel through the lumen 3, or alternatively, a catheter can be placed through the vascular sheath 1 and hemostatic valve 8 to the location of the obstruction and the material could be aspirated through the catheter. Thus, the vascular sheath 1 could be inserted into the blood vessel in a retrograde position, the extensions 11 deployed to occlude the blood vessel and blood clots, emboli and other materials could be aspirated from one side of the blood vessel, followed by partial deployment of the extensions 11, repositioning of the vascular sheath 1 to an antegrade position, re-deployment of the extensions 11 to occlude the blood vessel, and aspiration of and blood clots, emboli and other materials on the other side of the blood vessel.

When the vascular sheath 1 is used to insert a stent or perform angioplasty, the extensions 11 are also preferably deployed until they obstruct the vessel. A wire is used to cross through the obstruction. Then the stent is deployed or angioplasty performed, thus opening the blood vessel. During the manipulation of the wire and stent it is possible to withdraw blood, blood clots, and debris by aspiration through side arm 14. Alternatively, the aspiration can take place after the stent has been deployed or using a Fogarty balloon to pull debris out through the sheath. This would be determined by the location of the sheath relative to the lesion (i.e. upstream vs. downstream).

The size of the extensions 11 is not particularly limited. For example, when the device is used within a blood vessel, the deployed cross section of the extensions 11, as measured perpendicular to the length of the tubular portion, can range from just larger than the incision through which the tubular portion 2 was inserted into the blood vessel to as large as the inner diameter of the blood vessel. When used on other anatomical structures, the deployed cross section of the extensions 11 may vary and is limited only by the size of the anatomical structure and the particular requirements of the procedure. Preferably, so that the device can be used for various procedures requiring various deployment sizes, the extensions 11 are deployable to any size in between its retracted size and its maximum deployed size by simply controlling the amount of deployment and retraction of the extensions 11.

A side-arm 14 in fluid communication with the lumen 3 may also be located near the proximal end 4 of the tubular portion 2. The general features of the side-arm 14 are not particularly limited and may be in accordance with side-arms of conventional vascular sheaths.

The side-arm 14 can be used to allow air, emboli, blood clots and other materials to be evacuated from the anatomical structure through the tubular portion 2 and to allow agents, such as medicaments, anticoagulants and contrast media to be injected into the tubular portion 2 if desired. A stopcock 28 or similar mechanism is preferably attached to the end of the side arm 22 to selectively provide a seal.

When the side-arm 14 is used to aspirate emboli, blood clots and other materials from the anatomical structure, the side-arm 14 and stopcock 28 preferably has an inner diameter at least as large as the lumen 3 of the tubular portion 2 so that materials aspirated through the tubular portion 2 fit through the side-arm 14 and do not become lodged at the opening of the side-arm 14.

In some embodiments, the device of the present invention could be inserted in a target blood vessel or anatomical structure, and also connected to a recipient blood vessel or anatomical structure. For example, the device may be inserted into a blood vessel and also connected to another blood vessel, usually a vein, by either a surgical cutdown or using a percutaneous technique. This embodiment would effectively create an arterial venous shunt/circuit. For example, in one embodiment, the tubular portion of the device is inserted in the target anatomical structure and the side-arm 14 is connected to a recipient anatomical structure, thereby creating a continuous flow reversal circuit from the target anatomical structure, through the distal end of the tubular portion, through the tubular portion, through the side arm, and into a target anatomical structure.

Such a continuous flow reversal circuit would require access to the recipient anatomical structure. For example, in some embodiments, the side arm 14 could be directly inserted in the recipient anatomical structure. In other embodiments, the side arm 14 or another portion of the device could be connected to tubing that is inserted in the recipient anatomical structure. In other embodiments, the device of the present invention is connected to a recipient anatomical structure via a conventional guide catheter or conventional vascular sheath. In other embodiments, the side arm 14 or another portion of the device of the present invention is connected to a second device in accordance with the present invention such that the tubular portion of the first device is inserted in the target anatomical structure and the tubular portion of the second device is inserted into the recipient anatomical structure. The first and second devices are connected to each other, for example, via the side arms 14 of each device or, for example, via the hemostatic valves 8 of each device through tubing connecting the two hemostatic valves 8 together.

Such continuous flow reversal would be useful, for example, in performing a procedure wherein materials, for example emboli, blood clots, or blood, are transferred from a donor blood vessel into a recipient blood vessel. The device of the present invention could be used to occlude a donor vessel and prevent emboli, blood clots and other materials from propagating into the cerebral or coronary vasculature. The emboli, blood clots and other materials could then be transferred to a recipient blood vessel wherein the danger of having the materials propagate into the cerebral or coronary vasculature is eliminated. In addition to occluding the donor vessel, the mechanism would prevent the device from being pulled from the donor vessel during the transfer. In this embodiment, the device would be inserted in the donor blood vessel and, a continuous flow reversal could be created by forming a circuit between the "donor" vessel housing the embolic material to a "recipient" vessel elsewhere in the body. Vascular access to the recipient vessel would then be provided, for example, via the side arm 14, a tube, a guide catheter, a vascular sheath or another device in accordance with the present invention. In some embodiments, a pumping mechanism is interposed in the circuit between the donor and recipient vessels to assist in reversing the blood flow.

Preferably, during the continuous flow reversal procedure, the balloon (s) 10 or extensions 11 could be retracted or partially refracted at any point in the procedure to allow reperfusion of blood flow through the blood vessel. Then, if desired, the transfer of materials from the donor to recipient blood vessel could be reestablished at any point simply by again deploying the balloon(s) 10 or extensions 11 to occlude the vessel.

The continuous flow reversal described above could also be useful in a procedure wherein blood is transferred from one patient to another or from one site to another in the same patient as in cardiac bypass surgery. In such procedures, the device of the present invention, for example, in the form of a vascular sheath or guide catheter, would be inserted into a donor patient's vessel. The device of the present invention would then be connected to a recipient patient's vessel via, for example, a tube, conventional guide catheter, conventional vascular sheath, or second device in accordance with the present invention. The device of the present invention would be particularly helpful on preventing the loss of vascular access during the blood transfer procedure.

While continuous flow reversal is described, in particular, wherein the mechanism (e.g. balloon(s) 10 or extensions 11) are deployed to occlude the vessel, thereby preventing the flow of emboli, blood clots and other materials through the donor vessel, the mechanism could be retracted or partially deployed so as to not occlude the vessel wherein the danger of emboli, blood clots and other materials flowing through the donor anatomical structure is minimal. For example, in some embodiments, the mechanism is only partially deployed so as to prevent the device from losing access to the anatomical structure.

The hemostatic valve 8 is located at the proximal end 4 of the tubular portion 2, as shown in the Figures. The general features of the hemostatic valve 8 are not particularly limited and may be in accordance with hemostatic valves of conventional vascular sheaths.

The hemostatic valve 8 prevents leakage of blood and materials out of the anatomical structure through the device. In some embodiments, the hemostatic valve 8 can also be used to remove materials aspirated out of the anatomical structure. Preferably, when used to remove materials aspirated out of the anatomical structure, the hemostatic valve 8 is removably mounted on the proximal end 4 of the tubular portion 2 to facilitate removal of materials out of the proximal end 4 of the tubular portion 2. Thus, the hemostatic valve 8 could be removed after insertion and positioning of the device and inflation of the balloon 10 or deployment of extensions 11 and materials aspirated directly out of the proximal end 4 of the tubular portion 2. While the hemostatic valve 8 may be permanently mounted on the proximal end 4 of the tubular portion 2 and materials can be aspirated and removed through the hemostatic valve 8, it is generally easier to remove these materials through the proximal end 4 of the tubular portion 2 after removal of the hemostatic valve 8.

The hemostatic valve 8 can be removably or permanently mounted on the proximal end 4 of the tubular portion 2 with any conventional means such as, for example, using various adhesives, forming the tubular portion 2 and hemostatic valve 8 with threaded portions so that the hemostatic valve could be screwed on and off of the tubular portion 2, and by forming the hemostatic valve 8 to permanently or removably snap onto the tubular portion 2.

In one embodiment, rather than a single mechanism at or near the distal end 6 of the tubular portion 2, the device may further include a second mechanism at or near the proximal end 4 of the tubular portion 2. In this embodiment, both the proximal end 4 and the distal end 6 would be inserted into the anatomical structure. For example, the device may be inserted distal end 6 first into a blood vessel, followed by insertion of the proximal end 4 into the blood vessel. A portion of the device between the two mechanisms would include one or more balloon inflation ports 12, in the embodiment where the mechanism for preventing the device from pulling out of the anatomical structure comprises one or more balloons 10. In embodiments where the mechanism for preventing the device from pulling out of the anatomical structure comprises one or more extensions 11, one or more deployment/retraction mechanisms are located along the portion of the device between the two mechanisms. The inflation port(s) 12 or deployment/retraction mechanism(s) would remain external to the blood vessel during use such that the mechanism for preventing the device from pulling out of the anatomical structure (balloons 10 or extensions 11) could be inflated/deployed and deflated/retracted at any point during the procedure. This type of an embodiment would be particularly suitable for use as a shunt. A typical procedure using such a device would include carotid endarectomy where the device would be inserted proximal and distal to the lesion to be operated on. The balloons 10 would be inflated to obstruct flow through the native vessel and flow through the shunt, around the lesion to be operated on and back into the native vessel, distal to the aforementioned lesion.

The use of the device of the present invention can be further understood from the following discussion and with reference to FIGS. 1-19. The following discussion relates to a device in the form of a vascular sheath used in connection with a blood vessel. However, it is to be understood that other types of devices for performing percutaneous and surgical interventions (e.g. guide catheters) may be used in a similar manner on various anatomical structures of the body.

The vascular sheath is generally used by the following procedure: the vascular sheath is prepared with the mechanism not deployed, i.e. the balloon 10 empty and preferably compressed about the tubular portion 2 or the extensions 11 retracted. An incision is made to provide access to the target site. For example, an incision may be made in the patient's upper thigh and a needle passed through the incision into the common femoral artery. A wire is passed through the needle into the artery and the needle removed, leaving the wire in place. The vascular sheath with dilator is inserted, distal end 6 first, over the wire into the blood vessel in the upper thigh. The dilator is then removed, leaving the sheath in place, inside the blood vessel. The vascular sheath is then directed to the target location. Preferably, the vascular sheath is inserted into the blood vessel in a retrograde position towards the patient's head. Indicia 24 can be used to determine the depth of insertion of the vascular sheath. The balloon 10, balloons 10a, or extensions 11 can then be inflated or deployed.

More specifically, techniques currently used for the insertion of small angiographic catheters is preferably utilized to insert the vascular sheath 1 (e.g. the Seldinger technique). See the *Journal of The American Medical Association*, Jan. 31, 1977, Volume 237.

If the surgeon wishes to aspirate blood clots, emboli or other materials out of the blood vessel, the balloon(s) 10, 10a or extensions are then inflated or deployed until the vessel is occluded. The vessel is known to be occluded when contrast injected through side-arm 14 into tubular portion 2 into the blood vessel is stagnant. An aspiration device can then be connected stopcock 28 on the side-arm 14 and the blood clots, emboli or other materials can be aspirated out of the blood vessel through the side-arm 14. In another embodiment, the blood clots, emboli or other materials can be removed through the hemostatic valve 8 by using a Fogarty balloon to pull the blood clots out of the blood vessel, into the sheath and out to the hemostatic valve 8. In another embodiment, the hemostatic valve 8 is removably mounted on the tubular portion 2. Thus, the hemostatic valve 8 is first removed from the proximal end 4 of the tubular portion 2 and the aspiration device is then attached to the proximal end of the tubular portion 2, so that the blood clots, emboli or other materials can be removed through the tubular portion 2 out the proximal end 4 or blood clots, emboli and other material pulled out of the vessel through the sheath by means of a Fogarty balloon. In another embodiment, the hemostatic valve 8 is removably mounted on the tubular portion 2. Thus, the hemostatic valve 8 is first removed from the proximal end 4 of the tubular portion 2. Then, a Fogarty balloon is used to pull clot out of the blood vessel through the tubular portion 2 out the proximal end 4 and the silicon pinch valve 40 is used to occlude the sheath once the Fogarty balloon has been removed and allow the user to re-attach the hemostatic valve 8 or silicone septum 46.

If the surgeon wishes to inject agents, such as medicaments, anticoagulants and contrast media, into the blood vessel through the vascular sheath, the surgeon simply opens stopcock 28 and inserts a syringe or similar injection mechanism into the entrance of the side-arm 14 and injects the agent.

When using the vascular sheath to implant a stent in the blood vessel, the device functions as an embolic protection device. The balloon(s) 10, 10a or extensions 11 are typically inflated/deployed to occlude the blood vessel. A wire is passed through the lumen 3 of tubular portion 2 and across the narrowed or occluded blood vessel. The stent is mounted on an angioplasty balloon and is then advanced over the wire through the lumen 3 of the tubular portion 2 and positioned at the narrowed or occluded portion of the blood vessel. The location can be confirmed by injecting contrast medial through stopcock 28 of side-arm 14 into lumen 3 of the tubular portion 2 into the blood vessel. The stent is deployed by either using an inflation device to inflate the angioplasty balloon or by unsheathing a self-expanding stent. The surgeon can aspirate through stopcock 28 of side-arm 14 during this process in order to prevent distal emboli if the vascular sheath is upstream from the occlusion. Additionally, a tubing circuit can be created between connected stopcock 28 on the side-arm 14 and another vascular sheath placed in a recipient blood vessel, usually a vein. A pump would be interposed in this circuit to aspirate the blood clots, emboli or other materials, during the procedure, out of the target blood vessel through the side-arm 14, through the tubing, and then into the recipient blood vessel. (already stated above) Moreover, if it is necessary during the procedure to re-establish blood flow, as may be the case during a prolonged coronary intervention, the vessel segment can have the debris cleared via aspiration, the balloon can be deflated to allow reperfusion, and then the balloon can be re-inflated to allow continuance of the procedure. Alternatively, if the vascular sheath is downstream from the lesion, the surgeon can wait until the stent is deployed to aspirate any embolic material that has been trapped by balloon(s) 10, 10a or extensions 11.

If the surgeon wishes to reposition the vascular sheath from a retrograde to an antegrade position and vice versa, the surgeon simply inflates or partially deflates the balloon 10 or deploys or partially withdraws the extensions 11 until the tubular portion plus balloon(s) 10, 10a or extensions 11 are sized smaller than the inner diameter of the blood vessel but larger than the opening through which the vascular sheath entered the blood vessel. As such, the balloon(s) 10, 10a or extensions are sized to enable manipulation of the vascular sheath 1 within the blood vessel while preventing loss of vascular access. The surgeon then pulls the vascular sheath back towards the opening through which the vascular sheath entered the blood vessel, then upwards and partially out of the opening if necessary, and back into the blood vessel in the opposite position. Often the dilator and a guidewire will be placed through the vascular sheath and into the blood vessel to permit the safe re-advancement of the sheath well into the artery. Because the tubular portion 2 plus inflated balloon(s) 10, 10a or extensions 11 are larger than the opening through which the vascular sheath entered the blood vessel, they prevent the vascular sheath 1 from exiting the blood vessel and, thus, allow the surgeon to access antegrade and retrograde positions in the blood vessel in a single procedure through a single incision.

If the surgeon wished to use the device of the present invention for the treatment of hemodialysis access grafts, only one sheath would be required, as compared to the two sheaths that are currently used in conventional methods. Using the device of the present invention, the surgeon would introduce the sheath with the dilator in place into the graft using Seldinger technique towards the venous anastomosis. The balloon(s) 10, 10a or extensions 11 on the tubular portion 2 could be used to angioplasty any narrowing of the graft or blood vessels, and also could used to push any clots out of the graft, into the arm vein. The surgeon then pulls the vascular sheath back towards the opening through which the vascular sheath entered the blood vessel, then upwards and partially out of the opening if necessary, and back into the blood vessel in the opposite position, towards the arterial anastomosis. The vascular sheath could then be used for access towards the arterial limb. Additionally, the vascular sheath with dilator could be advanced over the wire to the arterial anastomosis. The balloon(s) 10, 10a would be inflated or the extensions 11 deployed and the vascular sheath pulled back towards the opening through which the vascular sheath entered the blood vessel, then upwards and partially out of the opening if necessary, and back into the blood vessel in the opposite position, towards the venous anastomosis. The balloon(s) 10, 10a will then be re-inflated to the diameter of the graft or the extensions re-deployed to the diameter of the graft and the vascular sheath used to push any clots out of the graft and into the vein.

If the surgeon wishes to transfer materials from a target or donor anatomical structure to a recipient anatomical structure, the device of the present invention could be used to create continuous flow reversal. For example, the device of the present invention could be used to transfer materials, such as blood, clots and embolic materials, from one blood vessel in a patient to another vessel in a patient. For example, the continuous flow reversal could be used to transfer materials, such as clots and embolic materials, from a target vessel where there is a risk that the materials will propagate to the cerebral or coronary vasculature to a recipient vessel wherein this risk is eliminated. Alternatively, the device of the present invention could be used to transfer blood and other materials from a donor patient's blood vessel to a recipient patient's blood vessel.

In this embodiment, the method would further involve providing access to the recipient anatomical structure. For example, the device of the present invention could be connected to tubing, to a conventional guide catheter, to a conventional vascular sheath, or to a second device in accordance with the present invention, which, in turn is inserted in the recipient anatomical structure. Still further, in some embodiments, the side arm 14 of the device could be directly inserted in the recipient anatomical structure.

During the continuous flow reversal, the mechanism may be deployed to occlude the vessel, for example, if there is a risk that clots and embolic material may propagate to the cerebral vasculature. Alternatively, the mechanism may be deployed not to occlude the vessel, but, rather, to maintain vascular access if, for example, there is minimal risk that clots and embolic material may propagate to the cerebral vasculature. If the mechanism is deployed to occlude the vessel, the method of continuous flow reversal may further include reperfusion of blood. For example, if reestablishment of the flow of blood to the heart is desired for a period of time during the procedure, the mechanism may be retracted during the procedure so that the vessel is no longer occluded and blood flow is reestablished. After perfusion of the blood is reestablished for a desired period of time, the mechanism may again be deployed to occlude the vessel. In some embodiments, during reperfusion, the circuit between the target blood vessel and recipient blood vessel can be blocked so that reperfusion is carried out while transfer of materials from the donor to recipient blood vessel is stopped. Then, after perfusion of the blood is reestablished for a desired period of time, the circuit may then be opened to continue transfer of materials from the donor to recipient blood vessel. During this time, the vessel may remain not occluded or may again be occluded by redeployment of the mechanism.

Upon completion of the procedure, the balloon(s) 10, 10*a* is deflated or the extensions 11 withdrawn and the vascular sheath 1 removed from the blood vessel.

It will be appreciated that the vascular sheath 1 is usable for any type of surgical procedure wherein a vascular sheath is needed to provide communication of medical devices with a patient's blood vessel, body organ, or body cavity.

The present invention also includes kits that comprise one or more device of the invention, preferably packaged in sterile condition. Kits of the invention also may include various sized tubular portions 2, balloons 10, 10*a*, extensions 11, side-arms 14, hemostatic valves 8, needles, dilators, etc. for use with the device, preferably packaged in sterile condition, and/or written instructions for use of the device and other components of the kit.

All documents mentioned herein are incorporated by reference herein in their entirety.

The foregoing description of the invention is merely illustrative thereof, and it is understood that variations and modifications can be effected without departing from the scope or spirit of the invention as set forth in the following claims.

What is claimed is:

1. A method for performing a vascular percutaneous intervention comprising the steps of:
   (a) providing a first device comprising:
     a tubular portion, having a proximal end and a distal end, and a lumen extending from the proximal end to the distal end;
     a retractable mechanism near the distal end of the tubular portion, the retractable mechanism providing an increased cross section of the tubular portion when deployed and substantially no increase in cross section of the tubular portion when retracted;
   (b) inserting the tubular portion of the first device into a donor blood vessel distal end first in one direction with the retractable mechanism retracted;
   (c) deploying the retractable mechanism to a size that occludes the donor blood vessel;
   (d) connecting the first device to a recipient blood vessel;
   (e) transferring materials from the donor blood vessel, through the tubular portion of the first device, and into the recipient blood vessel;
   (f) partially retracting the retractable mechanism to re-establish blood flow through the donor blood vessel, wherein the retractable mechanism is partially retracted to a size larger than an opening through which the tubular portion entered the donor blood vessel, thereby preventing the device from losing vascular access;
   (g) optionally re-deploying the retractable mechanism to a size that occludes the donor blood vessel, and reestablishing the transfer of materials from the donor blood vessel into the recipient blood vessel; and
   (h) retracting the retractable mechanism and removing the tubular portion of the first device from the donor blood vessel,
   wherein at any time when the retractable mechanism is partially retracted to a size larger than the opening through which the tubular portion entered the donor blood vessel, pulling the device back out of the donor blood vessel while maintaining vascular access and pushing the device back into the donor blood vessel in a direction opposite the one direction, whereby the deployed retractable mechanism prevents the device from losing vascular access.

2. The method of claim 1 wherein the step of (d) connecting the first device to a recipient blood vessel comprises the step of connecting the first device to a tube and inserting the tube into the recipient blood vessel.

3. The method of claim 1 wherein the first device further comprises a side arm extending from near the proximal end of the tubular portion and the step of (d) connecting the first device to a recipient blood vessel comprises the step of inserting the side arm into the recipient blood vessel.

4. The method of claim 1 further comprising the step of providing a second device comprising a second tubular portion, having a proximal end and a distal end, and a lumen extending from the proximal end to the distal end and wherein the first device is connected to the recipient blood vessel via the second device, and the step of (d) connecting the first device to a recipient blood vessel comprises the step of inserting the second device into the recipient blood vessel and connecting the first device to the second device.

5. The method of claim 1, further comprising the step of interposing a pump between the first device and the recipient blood vessel, wherein the pump assists in aspirating materials from the donor blood vessel and into the recipient blood vessel, or visa-versa.

6. The method of claim 1, further comprising the steps of:
   after step (e) and prior to step (f) stopping the transfer of materials from the donor blood vessel into the recipient blood vessel; and
   when the retractable mechanism is deployed to a size that occludes the donor blood vessel, removing emboli, blood clots, debris and other materials from the donor blood vessel through the tubular portion, and/or injecting one or more agents into the donor blood vessel through the tubular portion.

7. The method of claim 6, wherein the step of removing blood clots, emboli and other materials from the donor blood vessel comprises connecting the first device to an aspiration device and aspirating blood clots, emboli and other materials out of the donor blood vessel, and/or using a Fogarty balloon to pull blood clots and other materials out of the donor blood vessel.

8. The method of claim 1, further comprising the steps of:
prior to step d), removing emboli, blood clots, debris and other materials from the donor blood vessel through the tubular portion, and/or injecting one or more agents into the donor blood vessel through the tubular portion.

9. The method of claim 8, wherein the step of removing blood clots, emboli and other materials from the donor blood vessel comprises connecting the first device to an aspiration device and aspirating blood clots, emboli and other materials out of the donor blood vessel, and/or using a Fogarty balloon to pull blood clots and other materials out of the donor blood vessel.

10. The method of claim 1, wherein the retractable mechanism comprises at least one inflatable balloon, and the step of (c) deploying the retractable mechanism comprises inflating the at least one balloon to a size larger than the opening through which the tubular portion entered the donor blood vessel.

11. The method of claim 10, wherein the step of inflating the at least one balloon comprises inflating the at least one balloon to an overall round or oval shape situated coaxial with the tubular portion.

12. The method of claim 10, wherein the step of inflating the at least one balloon comprises inflating the at least one balloon to a funnel-like shape coaxial with the tubular portion, with a larger cross-sectional end of the funnel-like shaped balloon positioned near the distal end of the tubular portion and a smaller cross-sectional end of the funnel-like shaped balloon positioned towards the proximal end of the tubular portion.

13. The method of claim 12, wherein the step of inflating the at least one balloon comprises inflating the at least one balloon until the larger cross-sectional end of the funnel-like shaped balloon is flush with the distal end of the tubular portion.

14. The method of claim 12, wherein the step of inflating the at least one balloon comprises inflating the at least one balloon until the larger cross-sectional end of the funnel-like shaped balloon protrudes in front of the distal end of the tubular portion.

15. The method of claim 10, wherein the step of inflating the at least one balloon comprises inflating the at least one balloon until the at least one balloon is flush with the distal end of the tubular portion.

16. The method of claim 10, wherein the step of inflating the at least one balloon comprises inflating the at least one balloon until the at least one balloon protrudes in front of the distal end of the tubular portion.

17. The method of claim 1, wherein the retractable mechanism comprises one or more extensions, and the step of (c) deploying the retractable mechanism comprises deploying the one or more extensions to a size larger than the opening through which the tubular portion entered the blood vessel.

18. The method of claim 17, wherein the step of deploying the one or more extensions comprises deploying the one or more extensions to form a funnel-like shape with a larger cross-sectional end of the funnel-like shape positioned near the distal end of the tubular portion and a smaller cross-sectional end of the funnel-like shape positioned towards the proximal end of the tubular portion.

* * * * *